United States Patent
Nikoonahad et al.

(10) Patent No.: US 7,369,233 B2
(45) Date of Patent: May 6, 2008

(54) OPTICAL SYSTEM FOR MEASURING SAMPLES USING SHORT WAVELENGTH RADIATION

(75) Inventors: Mehrdad Nikoonahad, Menlo Park, CA (US); Shing Lee, Fremont, CA (US); Hidong Kwak, San Jose, CA (US); Sergio Edelstein, Los Gatos, CA (US); Guoheng Zhao, Milpitas, CA (US); Gary Janik, Palo Alto, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 554 days.

(21) Appl. No.: 10/718,126

(22) Filed: Nov. 19, 2003
(Under 37 CFR 1.47)

(65) Prior Publication Data

US 2004/0150820 A1   Aug. 5, 2004

Related U.S. Application Data

(60) Provisional application No. 60/429,441, filed on Nov. 26, 2002.

(51) Int. Cl.
*G01N 21/17* (2006.01)
(52) U.S. Cl. .................. 356/369; 356/237.2; 356/625; 356/631; 356/636
(58) Field of Classification Search ............... 356/364, 356/630–632, 237.1–237.5; 250/559.27, 250/225
See application file for complete search history.

(56) References Cited

U.S. PATENT DOCUMENTS 5,608,526 A   3/1997   Piwonka-Corle et al.
5,712,701 A   1/1998   Clement et al.
5,747,813 A   5/1998   Norton et al.
5,883,710 A   3/1999   Nikoonahad et al.
6,118,525 A   9/2000   Fossey et al.
6,184,984 B1  2/2001   Lee et al.
6,215,551 B1  4/2001   Nikoonahad et al.
6,222,199 B1  4/2001   Freeouf
6,271,916 B1  8/2001   Marxer et al.
6,519,045 B2  2/2003   Kwon
6,813,026 B2  11/2004  McAninch
6,982,792 B1* 1/2006   Woollam et al. ............ 356/369

FOREIGN PATENT DOCUMENTS

WO   WO 99/45340   9/1999
WO   WO 00/65331   11/2000
WO   WO 02/50501   6/2002

OTHER PUBLICATIONS

"Optical Metrology Roadmap for the Semiconductor, Optical and Data Storage Industries", Woollam et al., Proc. of SPIE., vol. 4099, (Jul. 2000).*

(Continued)

*Primary Examiner*—Hoa Q. Pham
(74) *Attorney, Agent, or Firm*—Davis Wright Tremaine LLP

(57) ABSTRACT

In an optical system measuring sample characteristics, by reducing the amount of ambient absorbing gas or gases and moisture present in at least a portion of the illumination and detection paths experienced by vacuum ultraviolet (VUV) radiation used in the measurement process, the attenuation of such wavelength components can be reduced. Such reduction can be accomplished by a process without requiring the evacuation of all gases and moisture from the measurement system. In one embodiment, the reduction can be accomplished by displacing at least some of the absorbing gas(es) and moisture present in at least a portion of the measuring paths so as to reduce the attenuation of VUV radiation. In this manner, the sample does not need to be placed in a vacuum, thereby enhancing system throughput.

227 Claims, 16 Drawing Sheets

OTHER PUBLICATIONS

I'Spectroscopic Ellipsometry From the Vacuum Ultraviolet to the Far Infrared:, Woollam et al., Characterization and Metrology Por ULSI Technology: 2000 International Conference.*

"Characterization of Thin Films and Multilayers in the VUV Wavelength Range Using Spectroscopic Ellipsometry and Spectroscopic Photometry" Boher et al., 157 NM Symposium, (May 2000).*

"Materials Characterization in the Vacuum Ultraviolet With Variable Angle Spectroscopic Ellipsometry", Wagner et al., Phys. Stat. Sol. (a) 188, No. 4, (2001).*

"In Situ Monitoring of GaN Metal-Organic Vapor Phase Epitaxy by Spectroscopic Ellipsometry", Peters, J. App. Phys., vol. 88, No. 7, (Oct. 2000).*

"Ordinary and Extraordinary Dielectric Functions of 4H- and 6H-SIC From 3.5 to 9.0 EV", Lindquist et al., App. Phys. Lett., vol. 78, No. 18 (Apr. 2001).*

"Precise Charactreizationm of Resists and in the VUV Range for 157 NM Lithography", Bojer et al., Mat. Res Soc. Symp., vol. 636, (2001).*

"Notification of Transmittal of the International Search Report or the Declaration," for corresponding PCT Application No. PCT/US03/37939, International Searching Authority, European Patent Office, Jan. 10, 2004, 8 pages.

* cited by examiner

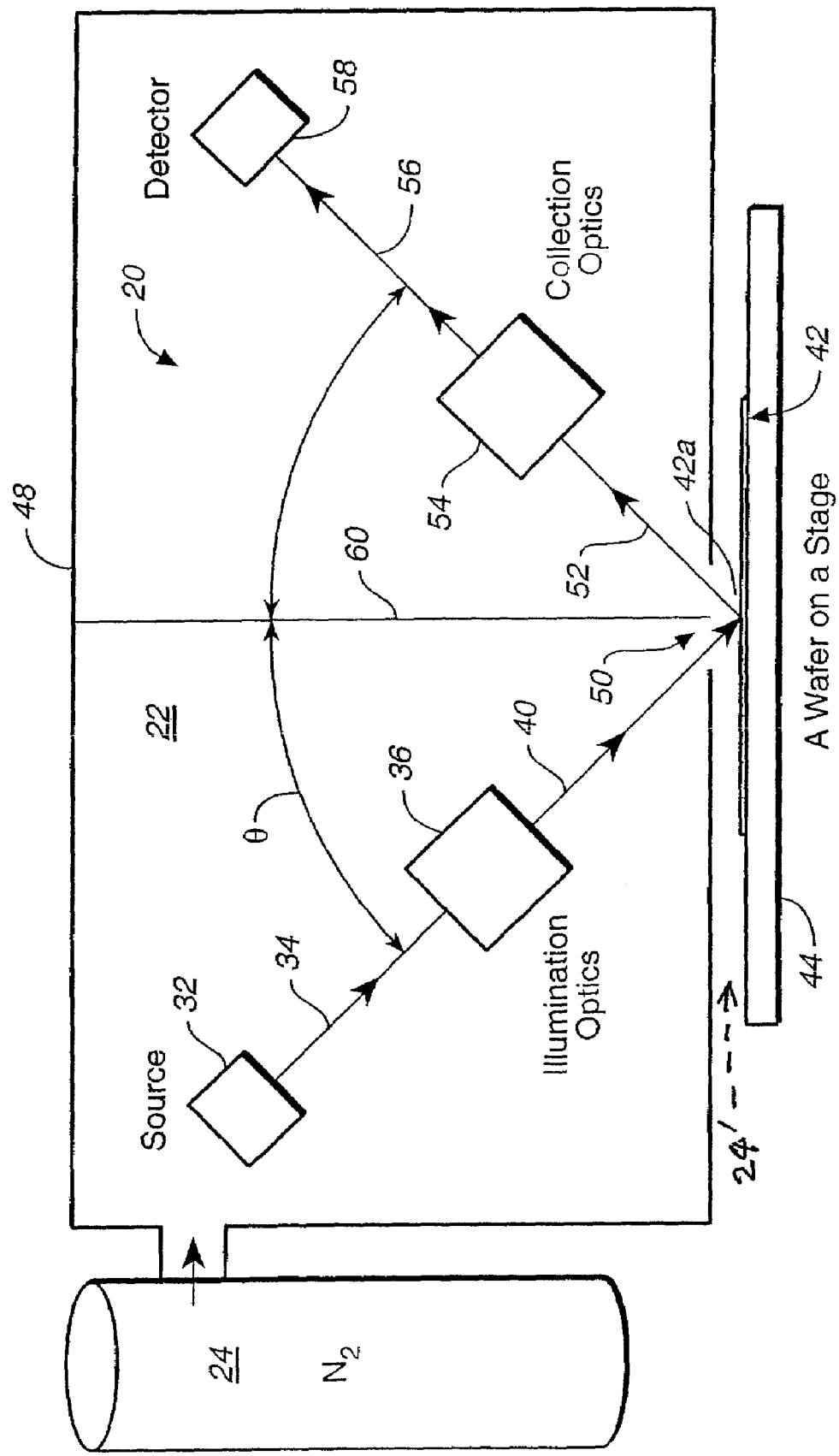
FIG._1

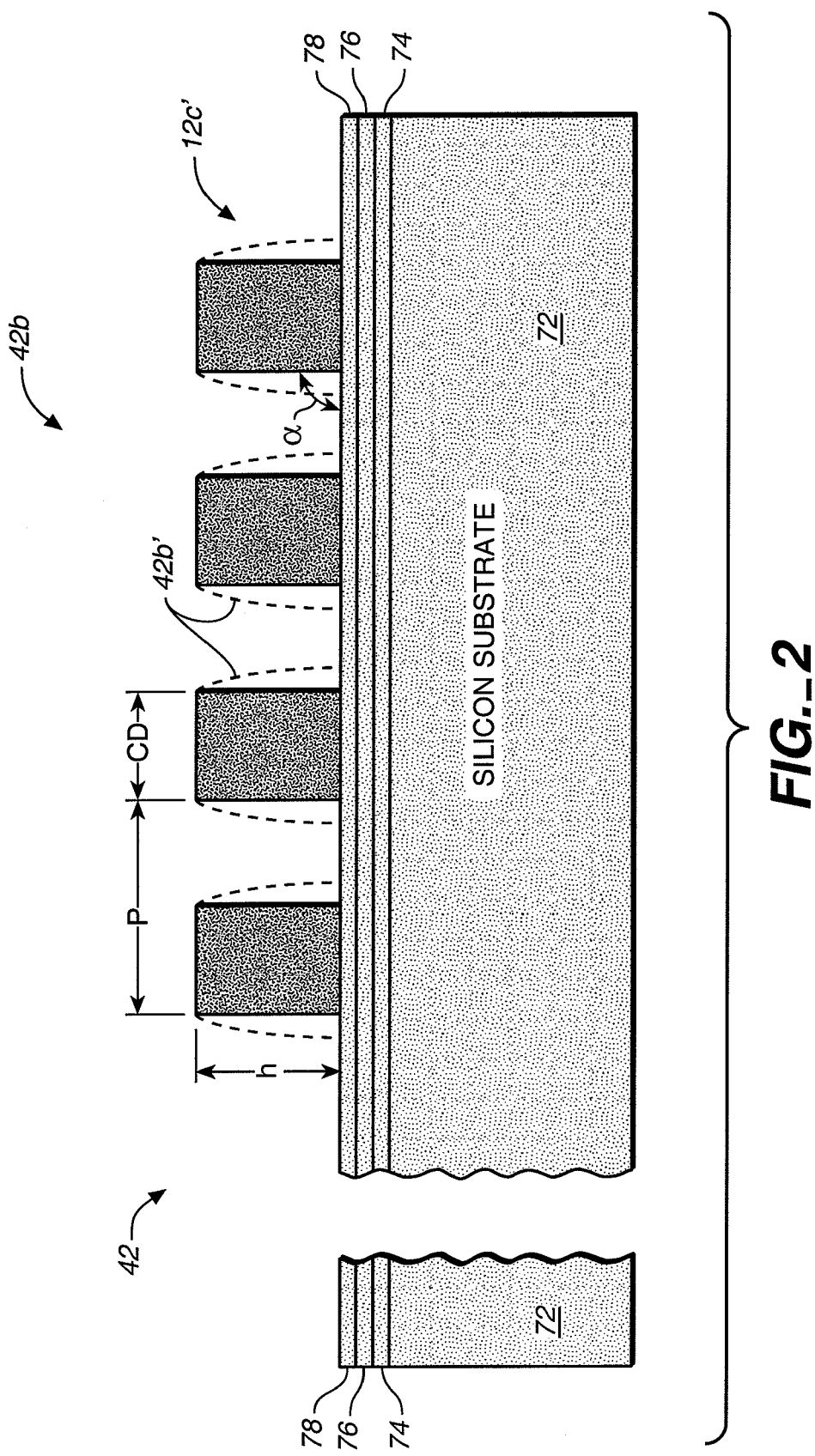
FIG._2

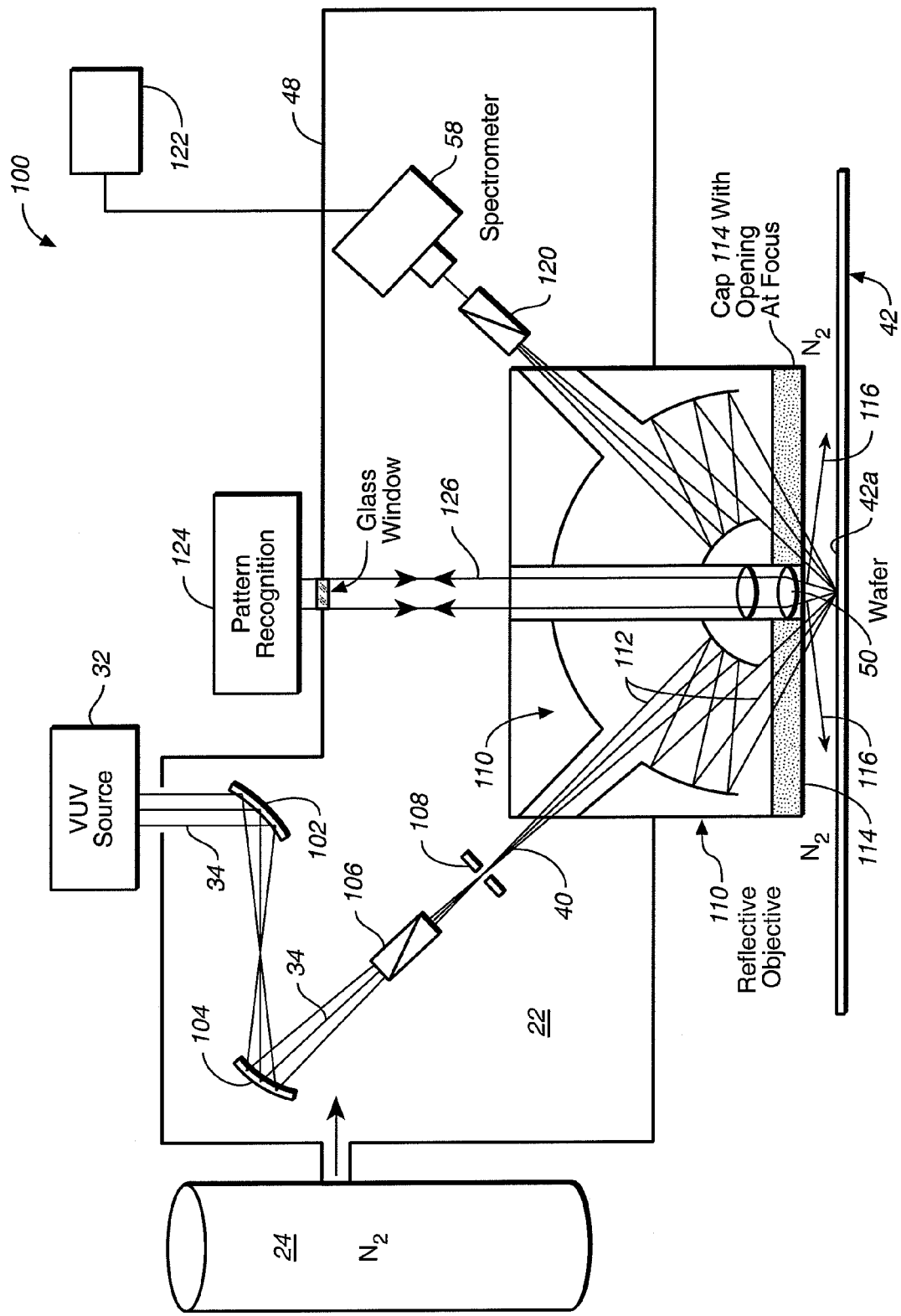
FIG._3

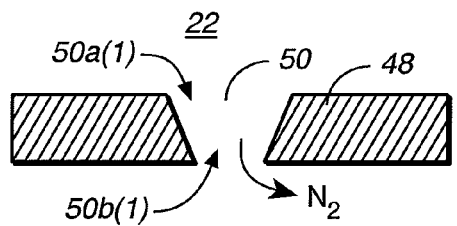
*FIG._4A*
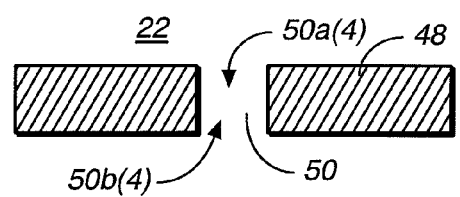
*FIG._4B*
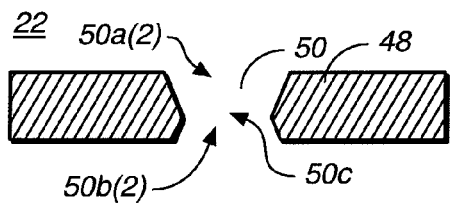
*FIG._4C*
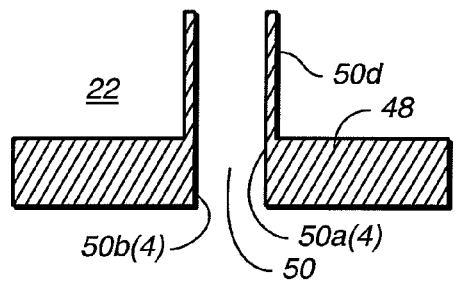
*FIG._4D*
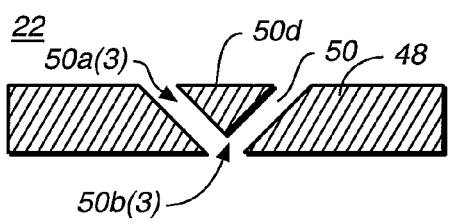
*FIG._4E*
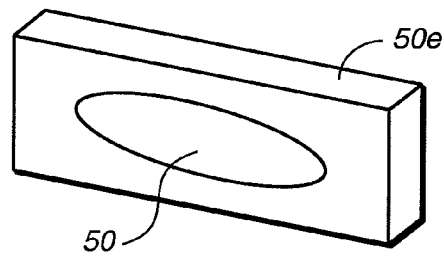
*FIG._4F*

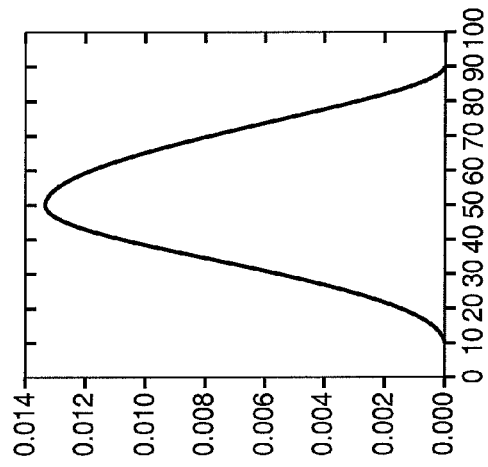
FIG._5C
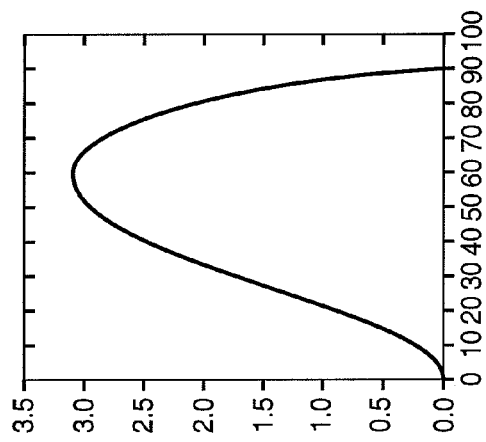
FIG._5B
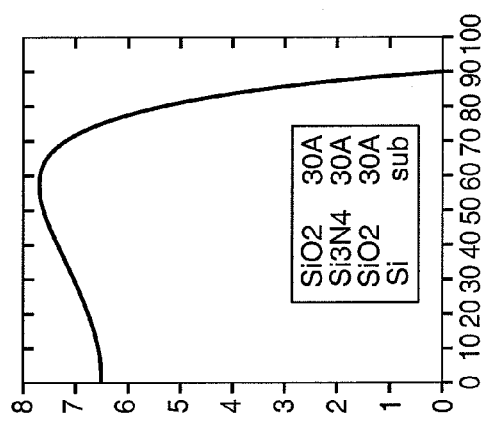
FIG._5A
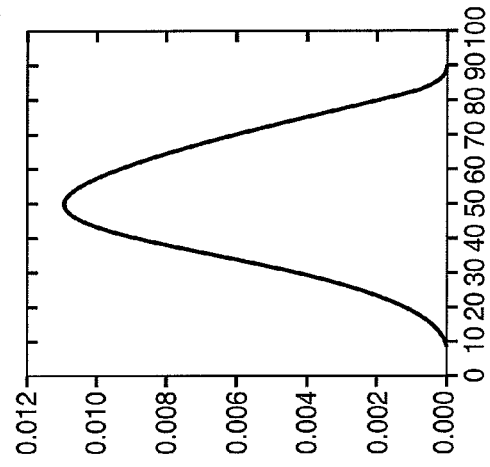
FIG._5F
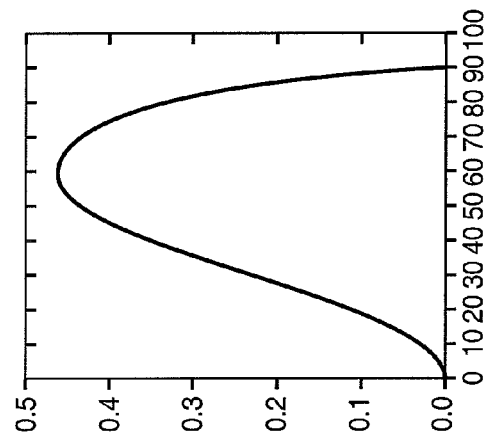
FIG._5E
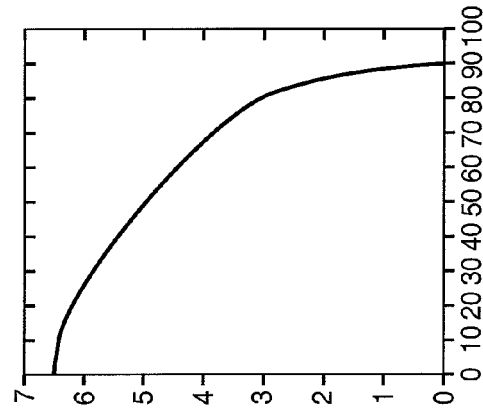
FIG._5D

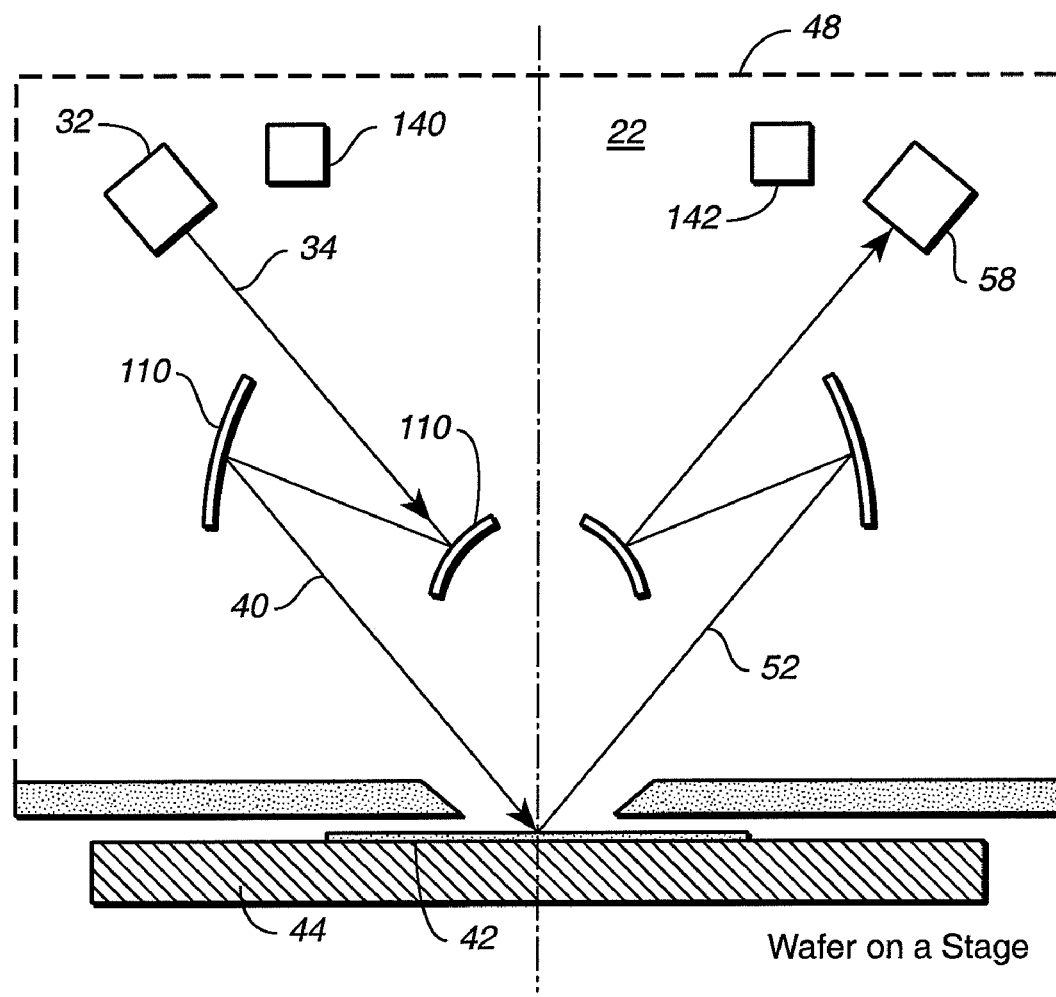
FIG._6

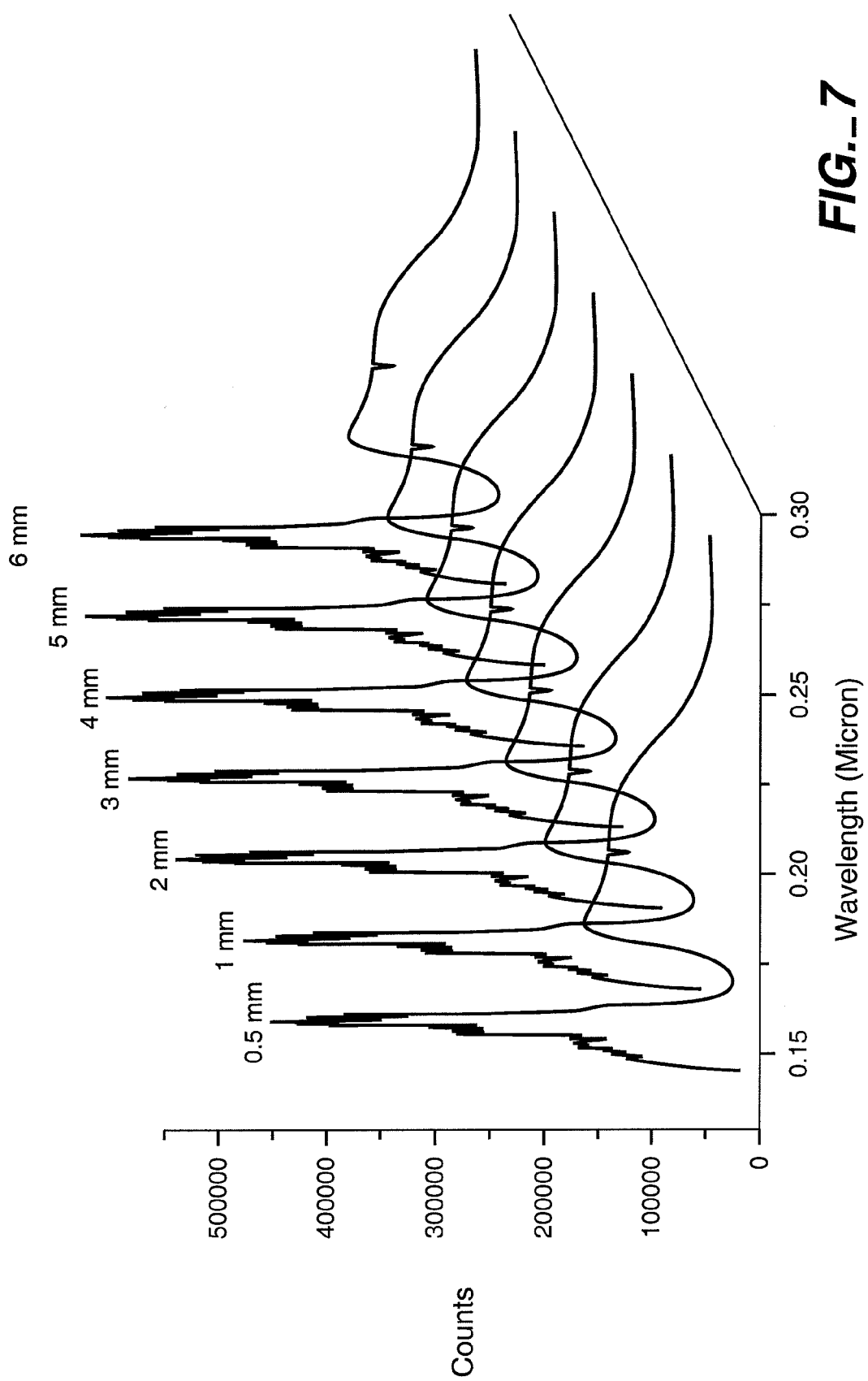
FIG._7

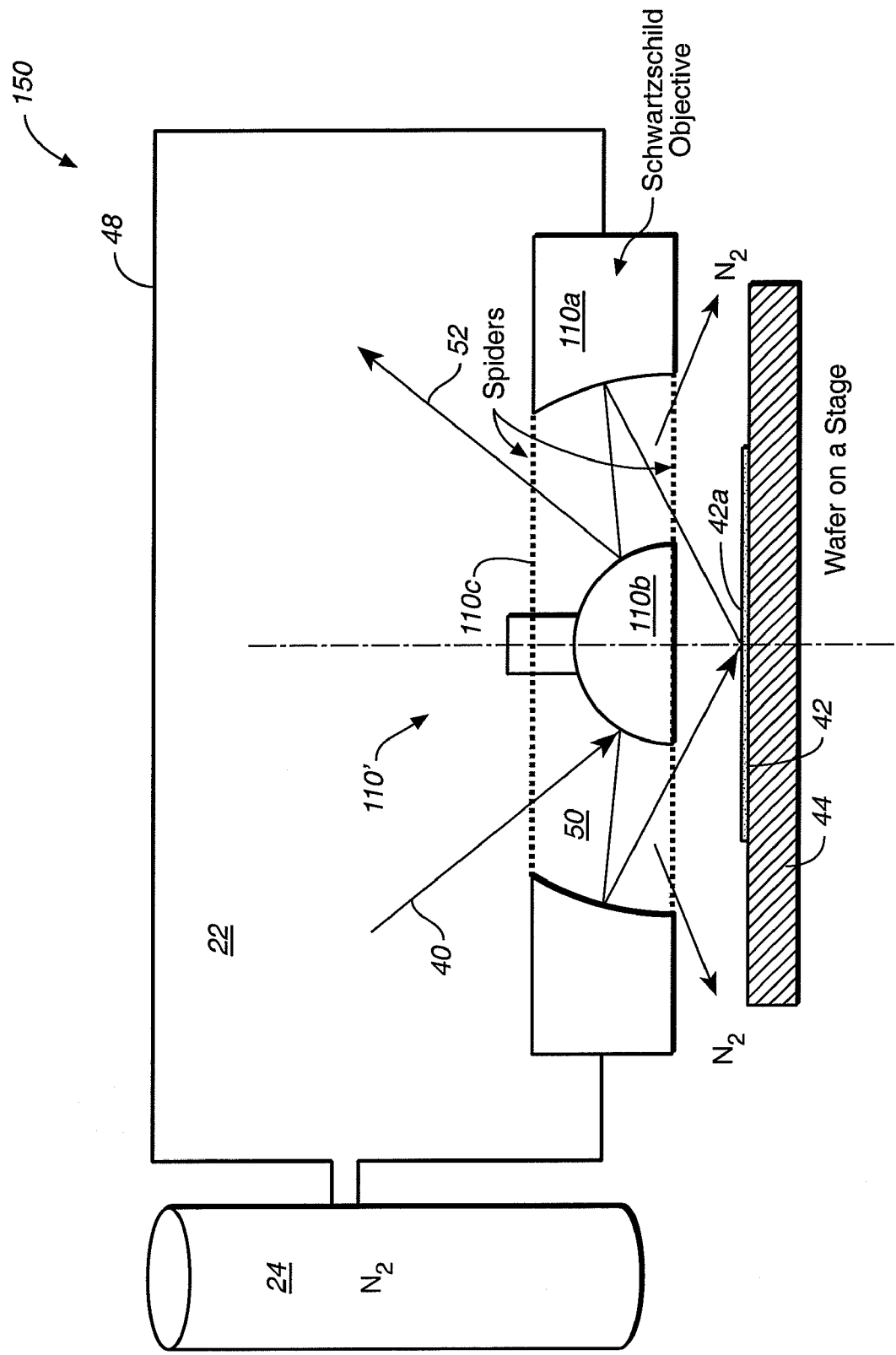
FIG._8

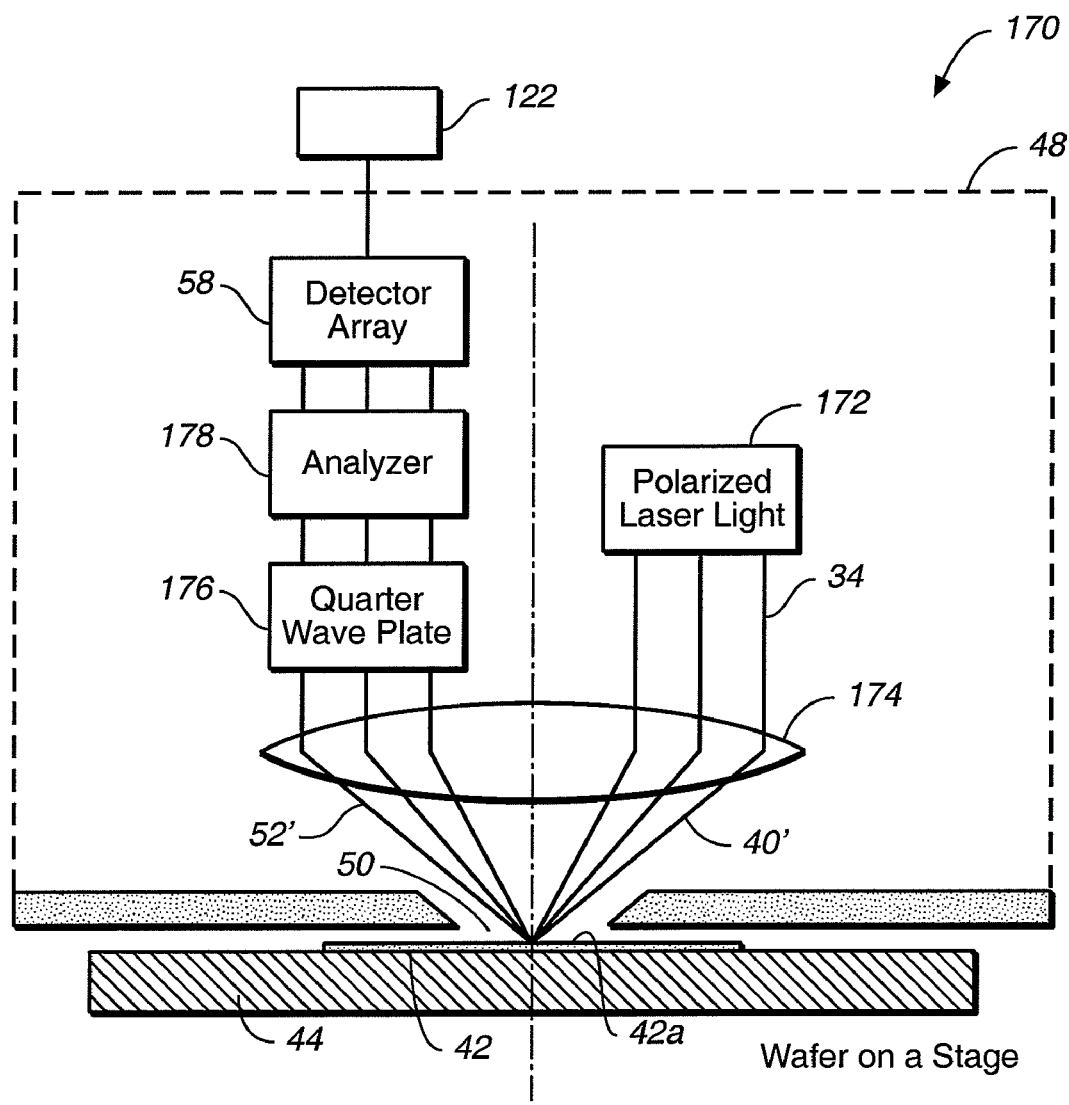
FIG._9

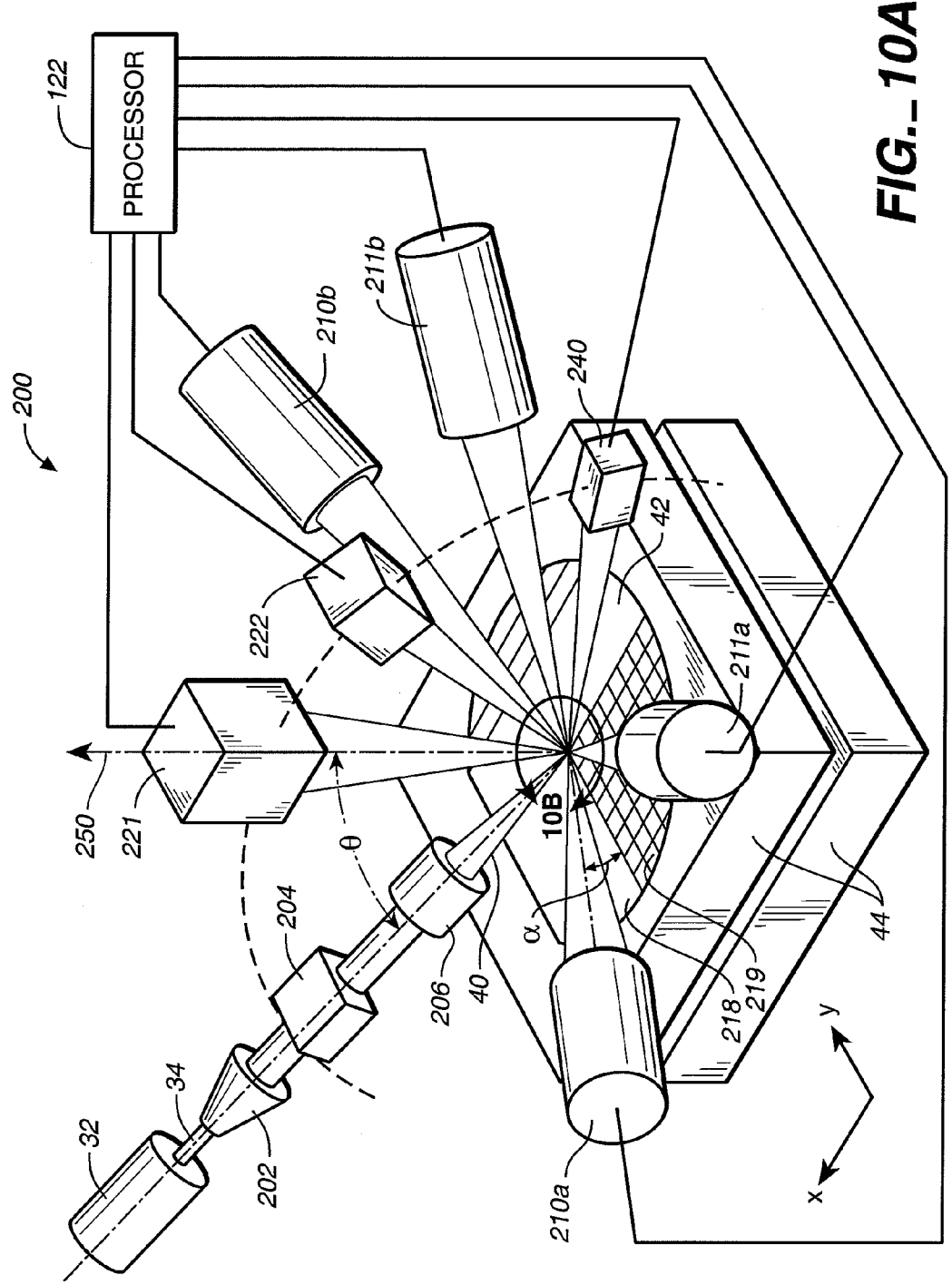
FIG._10A

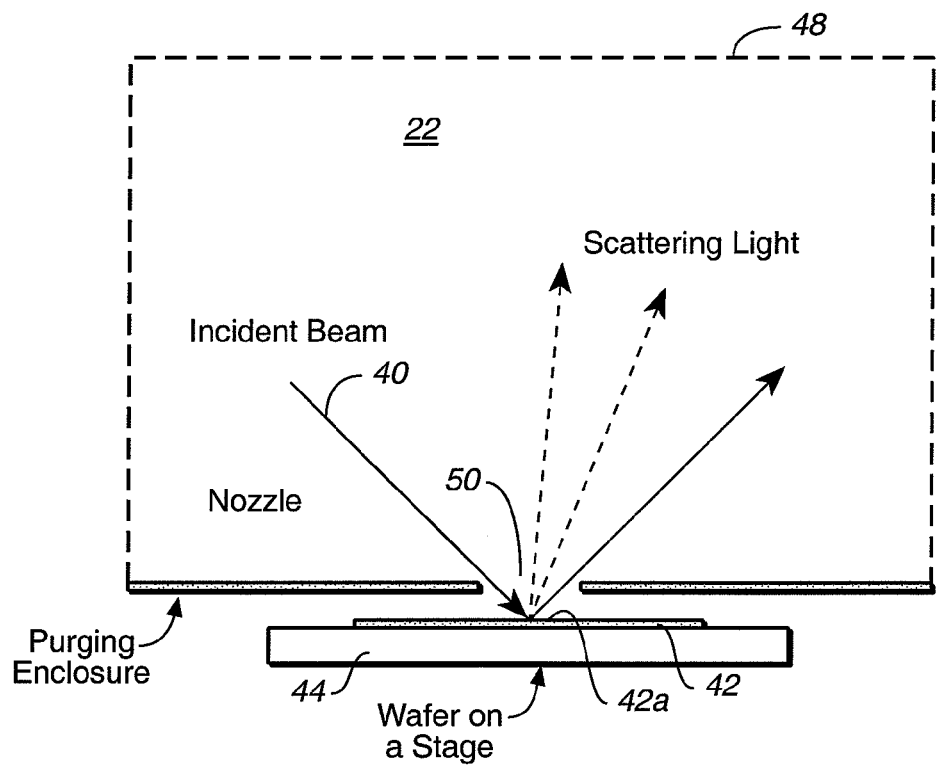
FIG._10B
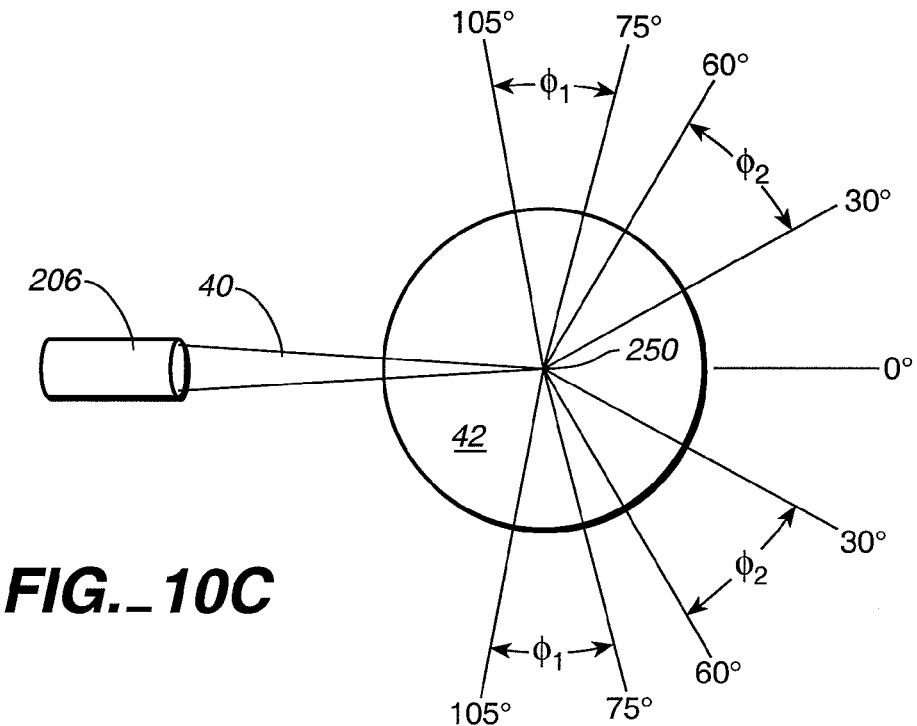
FIG._10C

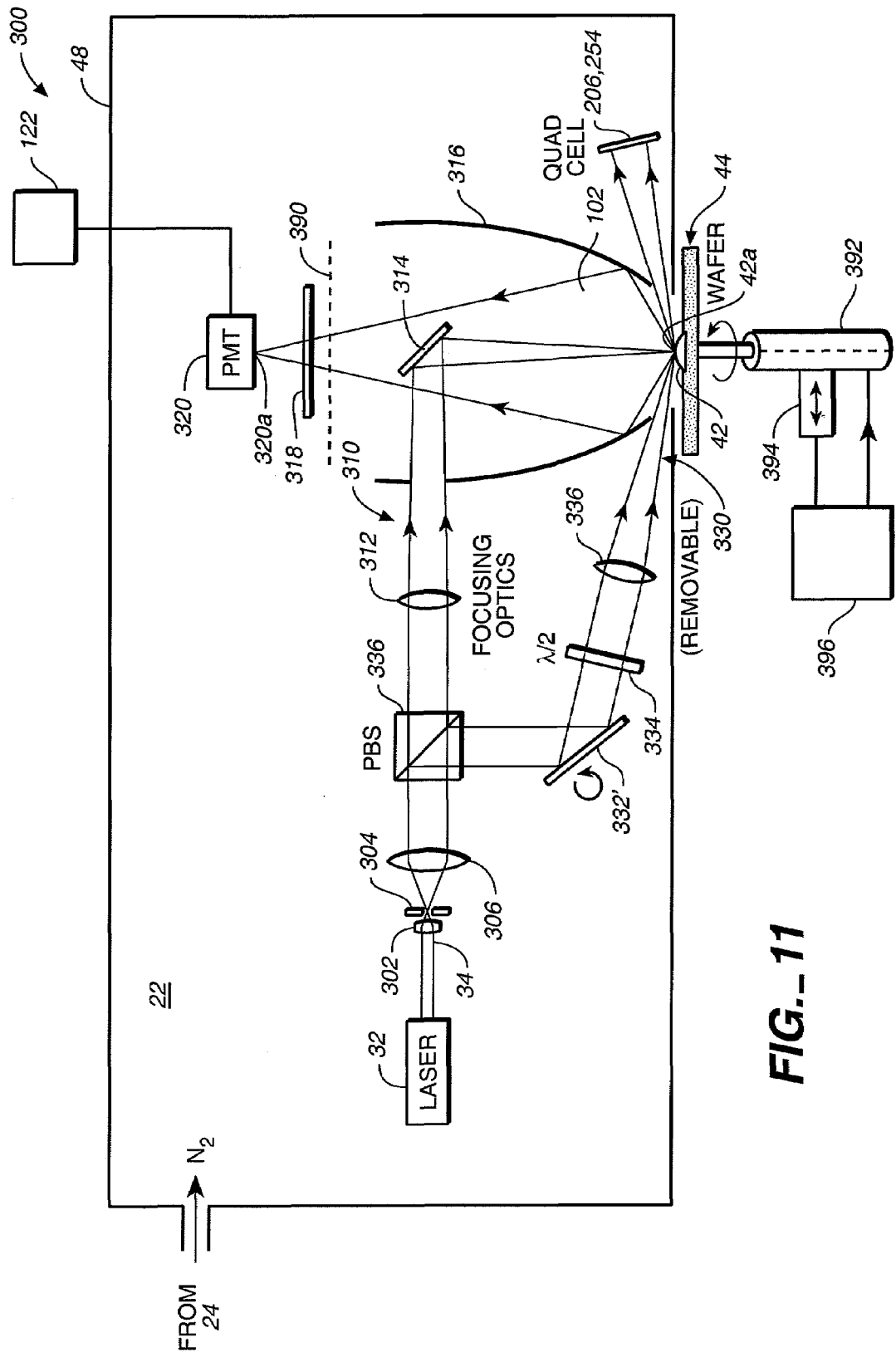
FIG._11

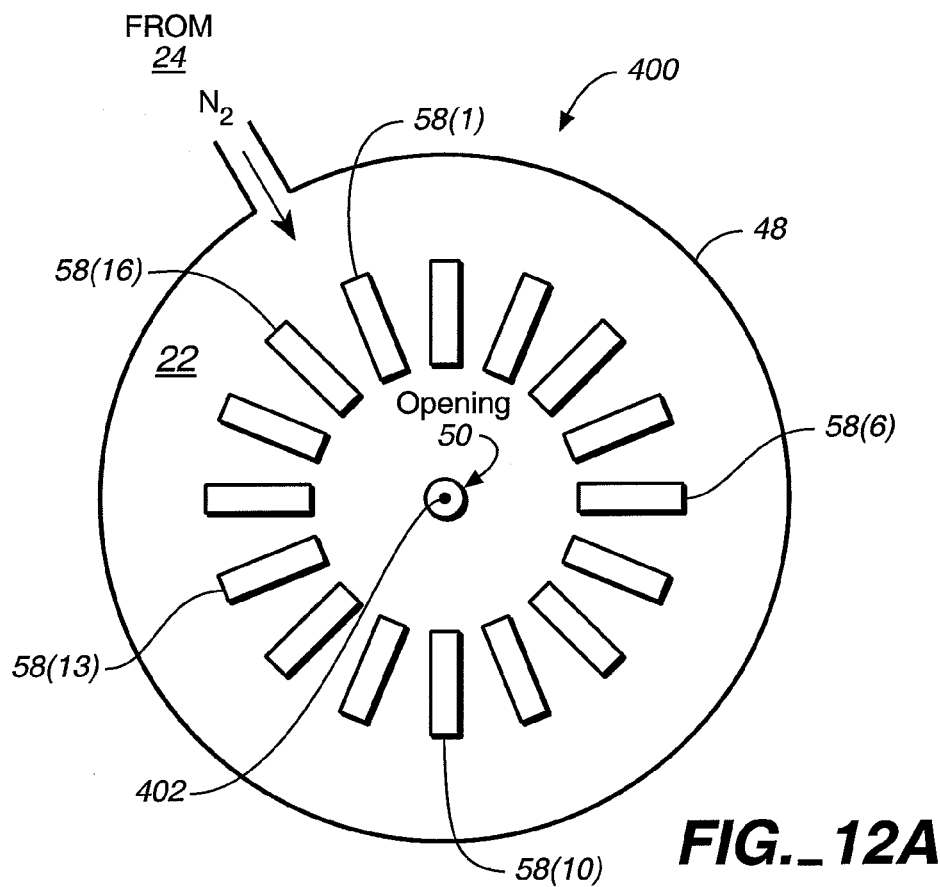
FIG._12A
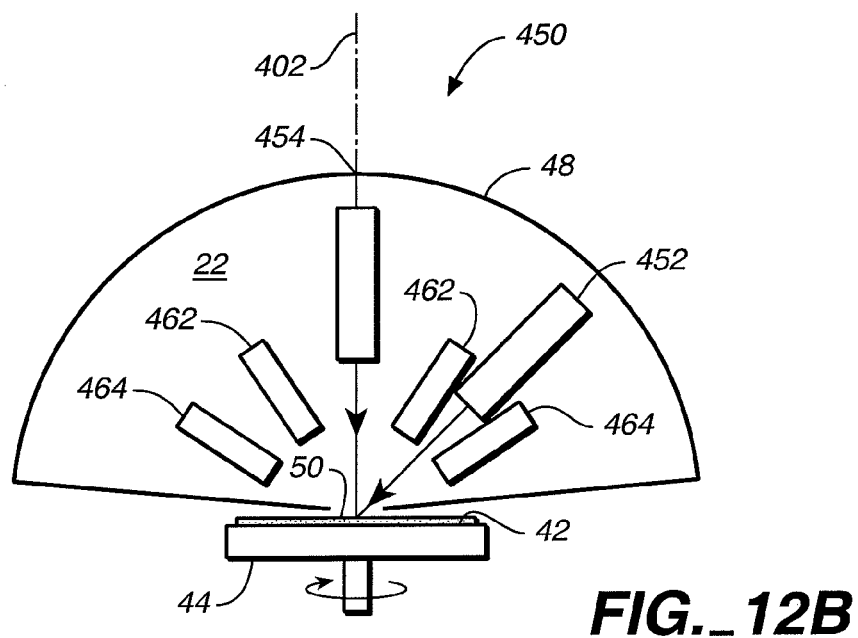
FIG._12B

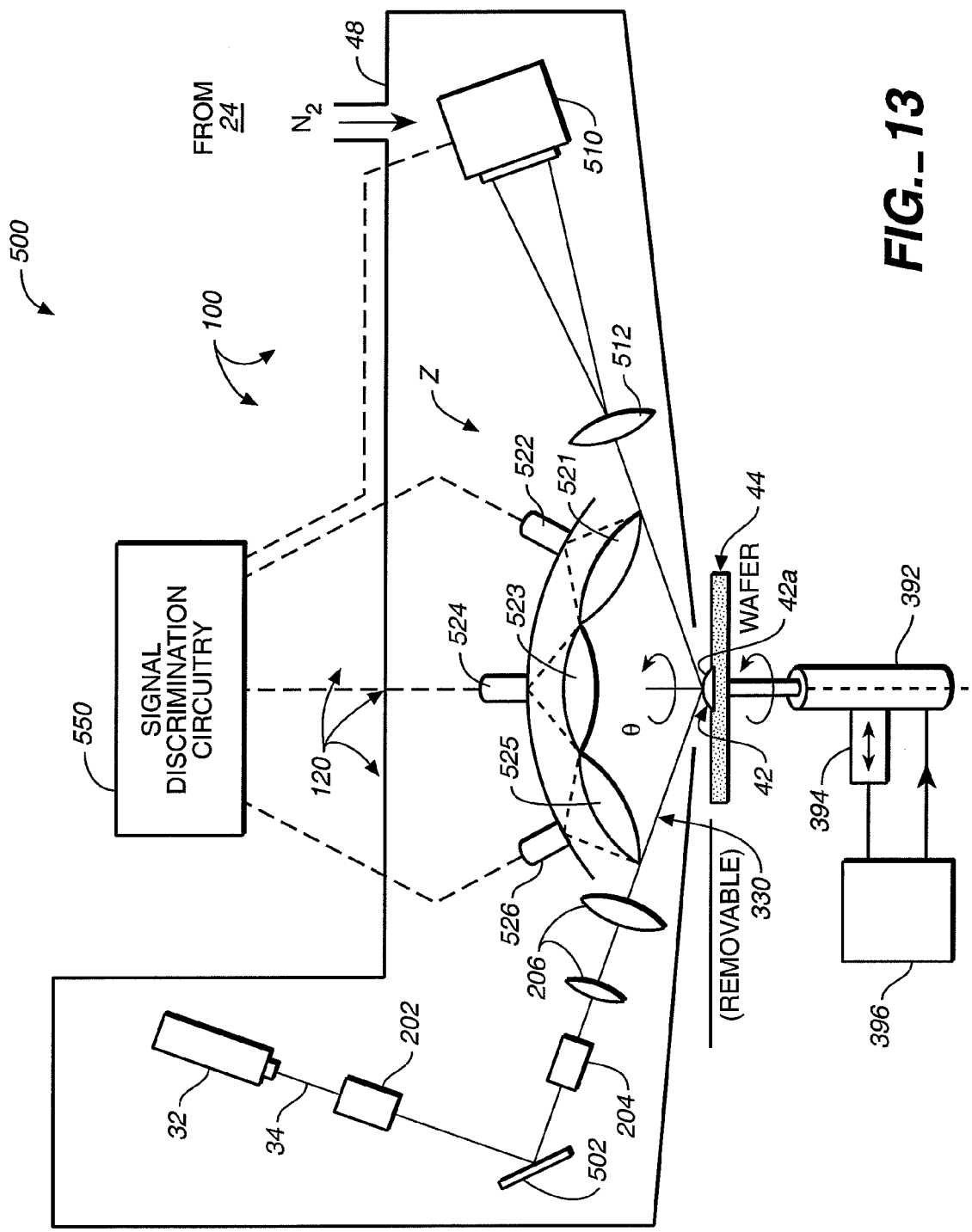
FIG._13

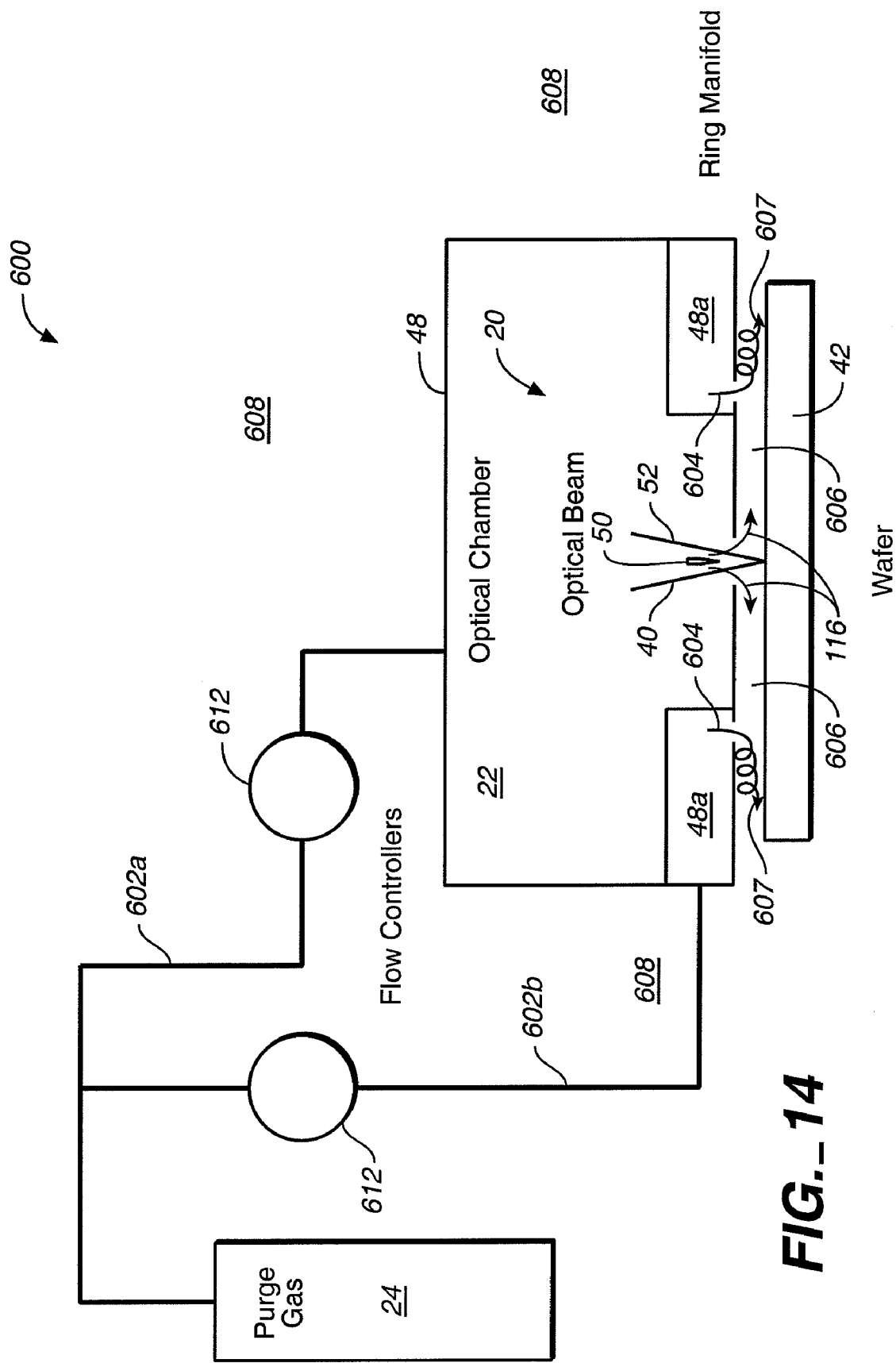
FIG._14

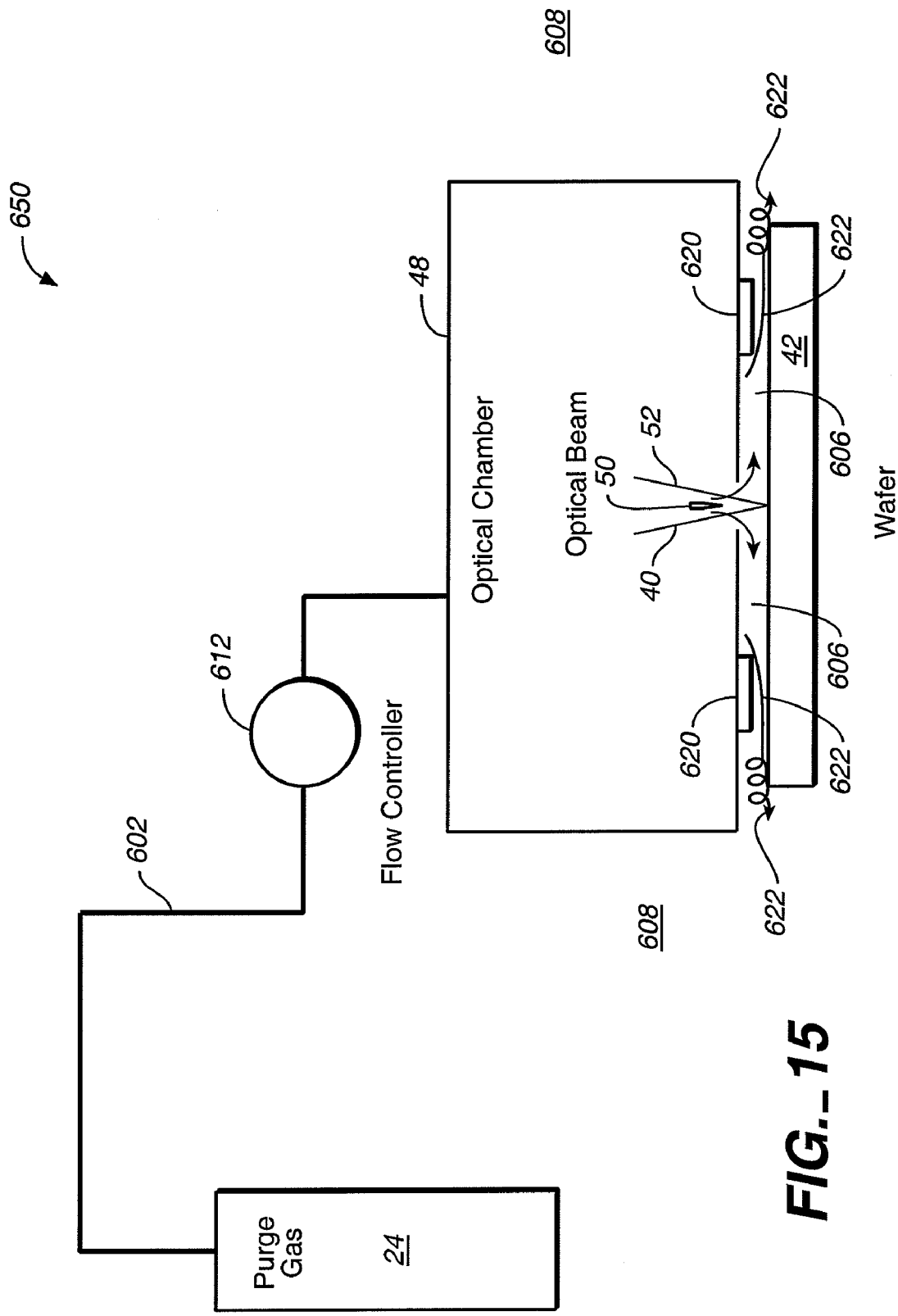
FIG._15

OPTICAL SYSTEM FOR MEASURING SAMPLES USING SHORT WAVELENGTH RADIATION

CROSS-REFERENCE TO RELATED APPLICATIONS

This application claims the benefit of U.S. Provisional Patent Application No. 60/429,441 filed on Nov. 26, 2002, which application is incorporated herein by reference.

BACKGROUND OF THE INVENTION

This invention relates in general to optical systems for measuring characteristics of a sample, and in particular to such system using radiation that contains a vacuum ultraviolet wavelength component.

For a number of industrial applications, it is useful to determine the surface metrology of samples such as thicknesses of thin films, their refractive indices and the profile parameters of surface features such as gratings on semiconductor wafers. These characteristics may be determined by a number of techniques. Among the better known non-destructive testing techniques are those of spectroreflectometry, spectroscopic ellipsometry and scatterometry.

With the shrinking of semiconductor devices to smaller and smaller geometries, the size of surface features such as gratings has also been continually reduced. For this reason, it is desirable to improve the sensitivity of instruments for measuring the metrology of samples.

In other industrial applications, it is useful to inspect samples to detect the presence of anomalies such as particles and surface and subsurface defects, such as anomalies associated with semiconductor wafers. To detect such anomalies, the sample surface is illuminated by means of electromagnetic radiation, and the radiation scattered or reflected by the sample surface is detected to determine the presence and classification of anomalies.

The size of semiconductor devices on silicon wafers has been continually reduced. The shrinking of semiconductor devices to smaller and smaller sizes has imposed much more stringent requirements on the sensitivity of wafer inspection instruments which are called upon to detect contaminant particles, pattern defects as well as defects of the surfaces that are small compared to the size of the semiconductor devices. At the time of the filing of this application, design rule of devices down to the order of 0.1 microns or below has been called for.

One approach to improve the sensitivity of metrology measurements and of anomaly inspection and detection is to employ electromagnetic radiation of shorter wavelengths such as ultraviolet wavelengths in the range of 140-180 nanometers. Ultraviolet light in this wavelength range is absorbed by oxygen and water molecules which are generally present in an ambient environment. As such, these short wavelengths do not propagate in air over an appreciable distance. For this reason, in order for radiation in this wavelength range to be used for measurements, measurements using such radiation take place in a vacuum or in purged gas such as nitrogen or argon. The ultraviolet light in this wavelength range is referred to as vacuum ultraviolet (referred to in this application as "VUV") radiation. Vacuum or fully purged gas measurement systems, however, are expensive to build. Furthermore, since the sample that is measured is also placed in the vacuum or purged gas, such systems typically have low throughput and are not suitable in manufacturing monitoring.

It is therefore desirable to provide measurement systems that can be used to measure sample characteristics using VUV radiation while avoiding the undesirable characteristics of vacuum systems.

SUMMARY OF THE INVENTION

This invention is based on the recognition that, by reducing the amount of ambient absorbing gas or gases and moisture present in at least a portion of the illumination and detection paths experienced by vacuum ultraviolet (VUV) radiation used in the measurement process, the attenuation of such wavelength components can be reduced. Such reduction can be accomplished by a process without requiring the evacuation of all gases and moisture from the measurement system. In one embodiment, the reduction can be accomplished by displacing at least some of the absorbing gas(es) and moisture present in at least a portion of the measuring paths so as to reduce the attenuation of VUV radiation. In this manner, the sample does not need to be placed in a vacuum or purged gas, thereby enhancing system throughput.

In one embodiment, the measurement system may be placed in a gas medium which contains less VUV absorbing gas(es) and moisture compared to an atmosphere surrounding the measurement system. Preferably, the gas medium is continually or continuously supplied by a source of gas that does not substantially absorb VUV radiation. In a preferred embodiment, this gas medium is maintained within an enclosure having an opening adjacent to the sample that is being measured. Preferably, the gas medium is maintained at a higher pressure compared to the ambient pressure so that the gas medium escaping through the opening reduces the amount of absorbing gas(es) and moisture that may otherwise be present in at least a portion of the measurement path of the VUV radiation passing through the opening between the measurement system, the sample and the detector. Also preferably, the opening is of such shape and size as to permit radiation to be incident on the sample at a range of different angles and enhances laminar flow of the gas through the opening while reducing turbulence, since turbulence may cause measurement errors.

To further reduce turbulence, preferably the region of the opening is shielded from the atmosphere, such as by another gas flow or an obstruction, so that the pressure differential that is maintained across the opening can be reduced. This further enhances laminar flow of the gas through the opening and reduces turbulence.

BRIEF DESCRIPTION OF THE DRAWINGS

FIG. 1 is a schematic diagram of a measurement system for measuring characteristics of a sample to illustrate an embodiment of the invention.

FIG. 2 is a cross-sectional view of a portion of a semiconductor wafer useful for illustrating the invention.

FIG. 3 is a schematic diagram of a system for measuring metrology of a sample to illustrate one application of the system of FIG. 1.

FIGS. 4A-4E are cross-sectional views of nozzles employed in the system of FIGS. 1, 3, 6, 8, 9, 10A-10C, 11, 12A, 12B and 13 to illustrate embodiments of the invention.

FIG. 4F is a perspective view of a portion of the system of FIGS. 1 3, 6, 8, 9, 10A-10C, 11, 12A, 12B and 13 showing a shape of a nozzle to illustrate another embodiment of the invention.

FIGS. 5A-5F are graphical illustrations of a measure of the radiation reflected by the sample versus the incident angle of the radiation useful for illustrating an aspect of the invention.

FIG. 6 is a schematic view of a portion of the system of FIG. 3 useful for illustrating the embodiment of FIG. 3.

FIG. 7 is a three dimensional graphical plot of the spectra obtained using the system of FIGS. 1 and 3 where a deuterium lamp is employed as the illumination source, useful for illustrating the invention.

FIG. 8 is a schematic view of another embodiment of the system of FIG. 1 useful for measuring the metrology of samples to illustrate another embodiment of the invention.

FIG. 9 is a schematic view of a metrology tool to illustrate yet another embodiment of the system of FIG. 1.

FIG. 10A is a perspective view of an inspection tool for detecting anomalies of samples to illustrate another embodiment of the system of FIG. 1.

FIG. 10B is a schematic view of a portion of the system of FIG. 10A.

FIG. 10C is a schematic view showing the azimuthal collection angles of four of the detectors of the inspection tool of FIG. 10A.

FIG. 11 is a schematic view of another inspection tool to illustrate yet another embodiment of the system of FIG. 1.

FIG. 12A is a top view of another inspection tool to illustrate yet another embodiment of the system of FIG. 1.

FIG. 12B is a side view of still another inspection tool to illustrate one more embodiment of the system of FIG. 1.

FIG. 13 is a partly cross-sectional and partly schematic view of an anomaly inspection tool to illustrate still another embodiment of the system of FIG. 1.

FIG. 14 is a schematic diagram of a measurement system for measuring characteristics of a sample to illustrate one more embodiment of the invention where laminar flow is enhanced.

FIG. 15 is a schematic diagram of a measurement system for measuring characteristics of a sample to illustrate a further embodiment of the invention where laminar flow is enhanced.

For simplicity, identical components are identified by the same numerals in this application.

DETAILED DESCRIPTION OF THE EMBODIMENTS

FIG. 1 is a schematic view of a measurement system for measuring characteristics of a sample such as a semiconductor wafer to illustrate one embodiment of the invention. As shown in FIG. 1, the optical measurement system 20 is placed inside an envelope 48. Hence, most of the optical beam path in system 20 is placed within a gas medium 22 that contains less moisture and absorbing gas with respect to VUV radiation compared to that in the ambient environment. In one embodiment, the gas medium 22 in envelope 48 comprises a nitrogen gas supplied by a nitrogen source 24 (which supplies a nitrogen gas that contains substantially no VUV absorbing gases such as oxygen and moisture). It will be understood that one or more other gases such as helium, argon, neon or another inert gas may be used instead or in combination with or without nitrogen and are within the scope of the invention. Preferably, the source supplies nitrogen gas to displace substantially all of the air and moisture that would affect the measurement process. For cost reasons, it may be desirable to use nitrogen rather than other suitable gases.

System 20 includes a radiation source 32 that provides radiation beam 34 that includes at least one VUV wavelength component. Radiation 34 is processed by illumination optics 36 to provide an illumination beam 40 to illuminate at least a portion of an area 42a of a sample 42 such as a semiconductor wafer that is supported on a stage 44. Preferably, the gas medium 22 is contained within an envelope or container 48 that has an opening 50 adjacent to area 42a of the wafer. In this manner, medium 22 contains less VUV absorbing gas(es) and moisture than an atmosphere surrounding the envelope. The illumination beam 40 passes through the hole or opening 50 to reach area 42a of the wafer as shown in FIG. 1. Radiation 52 that has been modified (such as scattered or reflected) by wafer 42 is then collected by collection optics 54, which provides the collected radiation in a beam 56 to detector 58. The output of detector 58 is supplied to an electronic device 62 for analysis. A positive pressure is maintained in the container 48 that the ambient gases and moisture is driven away by the outflowing gas from the container 48 through the opening 50. To speed up the displacement process of displacing the air and moisture originally present in the envelope 48, it may be desirable to at least partially evacuate envelope 48 and then fill it with nitrogen from source 24. Such a processes can be repeated a few times to shorten the purging time.

Thus, the illumination path of radiation beams 34 and 40 and the collection path of scattered or reflected radiation beams 52 and 56 as well as all of the optical elements shown in FIG. 1 are located in the most part within the gas medium 22 while only small portions of paths 40 and 52 at the opening 50 lie outside medium 22. Since medium 22 contains less absorbing gas that would absorb the VUV wavelength components and less moisture than the ambient atmosphere, the radiation in the illumination and collection paths of system 20 will therefore experience less absorption of the VUV wavelength components compared to where medium 22 is the atmosphere.

The fact that all the optical components of system 20 are placed in a suitable gas environment ensures that any water moisture absorbed by the surfaces of these components will outgas during the purging process when the envelope 48 is first filled with nitrogen gas. Moisture normally present on top of wafers can cause the measurement to unintentionally vary from time to time due to the condition of the wafer. The gas flow exiting from the opening can purge away the a few monolayers of moisture normally on top of the sample to improve the stability and accuracy of measurement.

Preferably, medium 22 is maintained at a higher pressure than the ambient pressure surrounding envelope or enclosure 48, so that a small amount of the gas medium 22 will leave the enclosure 48 through opening 50, thereby reducing the amount of absorbing gas such as oxygen and moisture that lie in the illumination and collection paths of radiation in the illumination beam 40 and the collected radiation 52 lying outside envelope 48. Source 24 supplies a stream of nitrogen gas continually or continuously to envelope 48 to replenish the nitrogen that has escaped through opening 50 from medium 22. In this manner, the amount of absorption experienced by the radiation in the illumination and collection paths of the radiation originating from source 32 and detected by detector 58 is further reduced or substantially eliminated.

Instead of having an opening 50, envelope 48 may be entirely or substantially sealed from the ambient environment. For example, it is possible to install a radiation transmissive or transparent window at opening 50 so that the nitrogen in medium 22 will not escape through the opening.

The measurement paths of the beams 40 and 52 will then pass through the window. The wafer is then kept at a very small distance (e.g. less than 100 microns) from the window, and the absorbing gas(es) and moisture present in the paths of the beams 40 and 52 near the wafer surface 42a are reduced by supplying nitrogen or another inert gas from a side location from a supply 24' shown as a dotted line arrow in FIG. 1 to displace such gas(es) and moisture, for example. The window is preferably calibrated to reduce any errors that may be caused by having the radiation in the optical paths pass through the window.

As shown in FIG. 1, since the wafer 42 is not located within the enclosure or envelope 48, the wafer may be freely moved by stage 44 while the optical components in measurement system 20 are preferably kept stationary, so that the throughput of the measurement system 20 is not impaired as is the case where the entire measurement, instrument and the wafer are enclosed in a vacuum or purged environment, which requires additional load-lock chamber and requires vacuum compatible wafer handlers and stages. This is particularly important for systems for inspecting anomalies on semiconductor wafers, so that system 20 may be used for in-line production use for both anomaly detection and metrology.

In FIG. 1, the illumination beam 40 is shown to be incident on the surface of area 42a at an oblique angle and therefore at angle θ to the direction or line 60 which is normal to the surface of area 42a. However, this is not required and beam 40 may be incident at the wafer in a direction substantially normal to the surface. The collected radiation 52 scattered in the normal or near normal direction may then be separated out, where necessary, by means of optical components in the collection optics, such as beam splitters, so that the collected radiation may then be provided to the detector 58.

METROLOGY APPLICATIONS

System 20 may be employed to measure the metrology of a sample, such as a semiconductor wafer 42 illustrated in FIG. 2. As shown in FIG. 2, wafer 42 comprises a silicon substrate 72 and three layers 74, 76 and 78, where one or more of the layers may comprise a material such as silicon dioxide, and other layer or layers may comprise silicon nitride. While only three layers of films are illustrated on the substrate 72, fewer or more layers of films may be present in sample 42; such and other variations are within the scope of the invention.

Apparatus 22 may be employed to measure characteristics of wafer 42, such as the thicknesses and indices of refraction of the layers, such as layers 74, 76 and 78. These characteristics may be measured by measuring the change in reflectivity, change of phase, or change of polarization state of polarized radiation caused by the sample or wafer 42. Thus, apparatus 22 may be a reflectometer or ellipsometer that can be used for measuring such parameters. As shown in FIG. 2, a grating structure 42b as part of the wafer pattern can be present on a portion of the surface of the wafer. While only four lines are shown in the grating 42b, it will be understood that typically gratings will include many more lines than four. Apparatus 22 may then be employed to measure the grating parameters such as pitch P, height h, critical dimension CD and a side wall angle α of the lines in grating 42b. Where the lines in grating 42b have more complicated profiles than simple rectangular cross-sections, such as indicated by the dotted line 42b', apparatus 22 may be employed to measure such profiles of the gratings 42b.

For details as to the techniques for measuring such grating profiles, see WO 02/50501, entitled "Parametric Profiling Using Optical Spectroscopic Systems," which is incorporated herein by reference in its entirety.

The measurement of the thickness and indices of refraction of layers 74-78 and of the grating parameters may be performed together or separately as described in PCT/US99/04053, Publication No. WO 99/45340, filed Feb. 25, 1999, entitled "Measuring a Diffracting Structure, Broadband, Polarized, Ellipsometric, and an Underlying Structure," which is incorporated herein by reference in its entirety.

FIG. 3 is a schematic view of an instrument 100 for measuring the metrology of a semiconductor wafer to illustrate one embodiment of the apparatus 20 of FIG. 1. As shown in FIG. 3, source 32 supplies radiation beam 34 that includes a VUV wavelength component. The radiation is focused by reflective objectives 102 and 104 and passes through an optical component a polarizer 106 and the slit in the spatial filter 108 and is focused by reflective objective 110 to area 42a of the wafer 42. The use of the reflective optic allows for a very broadband measurement. Refractive optics generally suffer from chromatic aberrations in a very broadband system. As will be noted in FIG. 3, even though the beam 112 that is focused by objective 110 to the wafer appears to pass through cap 114 adjacent to the opening 50, in fact it passes through the opening 50, which may be elliptical in shape as shown in FIG. 4F. Where medium 22 is maintained at a higher pressure than the ambient pressure outside the enclosure 48, the gas medium from medium 22 escaping through the opening or hole 50 will reduce the amount of ambient VUV absorbing gas and moisture that may be present in the path of beam 112. The paths of the nitrogen gas flowing out of medium 22 are illustrated by arrows 116. The nitrogen gas flow may also have the effect of removing at least some of the moisture and contaminants at or near the wafer surface 42a.

Radiation 52 from beam 112 that is reflected by the surface of area 42a is collected by objective 110, and the collected radiation is passed through an optical element 120 to a detector 58. For measuring a film stack with multiple layers, it may be desirable for source 32 to be a broadband source, to provide multiple wavelength components so that a large quantity of data (e.g. ellipsometric parameter data) may be provided across a spectrum to provide more information for determining the film thicknesses and indices of refraction of the films in the film stack. In such instance, detector 58 may be a spectrometer that separates out the various wavelength components that are reflected by the sample.

Where the film stack does not contain many layers and the layers are relatively thick, i.e., greater than a few thousand Angstroms, a spectroreflectometer may be adequate, such as one described in U.S. Pat. No. 5,747,813, which is incorporated herein by reference in its entirety. Where apparatus 100 is a spectroreflectometer, optical components 106 and 120 may be stationary polarizers or compensators such as wave plates, or they can be eliminated altogether. Where the film stack includes multiple films, it may be desirable for apparatus 100 to be a spectroscopic ellipsometer, such as one described in U.S. Pat. No. 5,608,526, which is incorporated herein in its entirety by reference. Where apparatus 100 is a spectroscopic ellipsometer, components 106, 120 may each comprise polarizers or compensators where one or both may be rotated when spectrometer 58 is detecting the reflected radiation from the wafer. More than one stationary and/or rotating polarizers or compensators may be employed in optics 106 and/or 120. Where a polarizer in optics 106 or analyzer in optics 120 is rotated, the phase shifts caused by the sample in the detector output in two orthogonal components may be compared to find a reference for measurement.

The wavelength components detected by spectrometer 58 are converted into electrical signals which are then provided to a device 122 for analysis. Device 122 may be a dedicated circuit made of programmable logic devices or field programmable gate arrays or one or more microprocessors for processing the data. Where apparatus 100 is an ellipsometer, device 122 also controls the rotation of devices 106 and 120 where such control lines are not shown to simplify FIG. 3. The pattern recognition block 124 supplies the radiation beam 126 for the positioning of the wafer 42 and for auto focusing so that beam 112 is properly focused onto the surface of the wafer. While for some applications, radiation 34 provided by source 32 may comprise multiple wavelength components, such as would be the case for broadband source 32, for other applications, a few or a single wavelength component may be adequate. In such event, detector 58 may comprise a photomultiplier tube or photodiode instead of a spectrometer.

FIGS. 4A-4F illustrate various different possible shapes of the opening or hole 50 in all different embodiments of this application. FIG. 4A is a cross-sectional view of a portion of the enclosure or envelope 48 adjacent to the hole or opening 50 to illustrate one embodiment of the invention. As shown in FIG. 4A, opening or hole 50 has two ends: an end 50a(1) which is within or close to medium 22 within the enclosure 48 and another end 50b(1) which is closer to the wafer 42 (not shown) than to the medium 22. As shown in FIG. 4A, end 50a(1) is larger in cross-section than end 50b(1), so that opening or hole 50 is funnel-shaped. When opening 50 is so shaped, the flow of nitrogen from medium 22 inside the enclosure through the opening is more likely to be laminar rather than turbulent. This is desirable since turbulent flow may cause fluctuation in the index of refraction of the medium for the beams 40 and 52 and causes noise in the measurement. Furthermore, such shape of the opening permits the angle of incidence of the illumination beam 40 to be at a greater angle to the normal line 60 than otherwise would be possible.

FIG. 4C illustrates another embodiment for the shape of opening 50. As shown in FIG. 4C, opening 50 has a middle portion 50c that is narrower in cross-section than the two ends 50a(2) and 50b(2). The opening 50 in FIG. 4E is similar to that shown in FIG. 4A except that a component 50d lies within the hole or opening. In certain embodiments, 50d may be an objective, such as illustrated in FIG. 8 described below. FIG. 5B is a cross-sectional view of a portion of the enclosure 48 and hole 50 to illustrate another embodiment of the hole 50. As shown in FIG. 4B, the hole 50 between its two ends 50a(4) and 50a(4) has a substantially uniform cross-section. In the embodiment of FIG. 4D, the hole 50 has essentially the same shape as that shown in FIG. 4B, except that a tube 50d is attached to the enclosure 48 near the end 50a(4) inside medium 22.

FIG. 4F is a perspective view of a portion of enclosure 48 to illustrate another embodiment of the invention. As shown in FIG. 4F, hole 50 is elongated in shape to permit a larger angle of incidence of beam 40 from the normal 60; preferably, hole 50 may be elliptical in shape as illustrated in FIG. 4F.

For certain materials in layers 74-78 and grating profile parameters, the output(s) of detector or spectrometer 58 vary with the angle of incidence of the illumination beam 40. Different film structures might have maximum sensitivity at different angles of incidences. For example, to detect film thicknesses and indices of refraction, the beam 40 illuminates the layers 74-78 at a location away from grating 42b. Where one of the layers 74-78 illuminated by beam 40 comprises silicon nitride, the different ellipsometric parameters as a function of the angle of incidence are illustrated in FIGS. 5A-5F. An optimal angle of incidence would be in the range of 50-60 degrees for the structure with sensitivity functions as shown in these figures. For this reason, it may be preferable to be able to vary and select the angle of incidence of the illumination beam 40 in order to increase or maximize sensitivity or the accuracy of the measuring the film structures. This may be accomplished by means of a motor as illustrated in FIG. 6. FIG. 6 is a schematic view of a portion of the system of FIG. 3 useful for illustrating the embodiment of FIG. 3.

As shown in FIG. 6, the source 32 and the illuminating optics 110 may be moved or rotated by a motor 140 to different locations so that the radiation beam 34 will be incident on objective 110 at different angles of incidence, thereby causing the illumination beam 40 incident on wafer surface 42a to be also at different angles of incidence to the surface of the wafer. When the angle of incidence of the illumination beam 40 changes, the detection path of the detected radiation 52 also changes. For this purpose, another motor 142 may be employed to move or rotate the detector 58 and the collection optics so that the detector may detect the collected radiation when the detection path of radiation 52 is changed. Alternatively, instead of moving source 32 and detector 58, it is also possible to move optical components that are in the path of the illumination beam 34, 40 or of the collector radiation 52, such as by moving mirrors 102, 104 of FIG. 3 by means of a motor (not shown in FIG. 3) or by moving a collection aperture (not shown in FIG. 3) such as in the manner described in U.S. Pat. No. 5,608,526, which is incorporated herein in its entirety by reference. The detector 58 may comprise a detector array so that at least some of the detectors in the array are positioned to detect the collector radiation 52 when the angle of the reflected radiation beam 52 changes due to a change in the angle of incidence of the illumination beam 40.

The ability to change the angle of incidence of the illumination beam 40 is also useful to provide more data points in scatterometric measurements of grating parameters. Thus, by changing the angle of incidence of the illumination beam 40 as described above, more data points may be provided in the measurement of reflectivity, film thickness, index of refraction and the grating parameters of the sample, where grating parameters comprise the critical dimension, side wall angle, pitch, height and/or profile of gratings.

The angle of incidence of a beam to a surface is the angle the beam makes with a direction or line normal to the surface. In one embodiment, the angle of incidence of beam 40 may be around 60°. The opening or hole 50 is close to the focal point of objective 110. In such arrangement, it is discovered that the output of detector 58 provides adequate output at the wavelength of interest when the wafer 42 is spaced from opening 50 by a wide range of distances, such as the range from about 0.5 to 6 millimeters as illustrated in FIG. 7. FIG. 7 is a three-dimensional graphical plot of the output of detector 58 over a spectrum of different wavelengths when the distance of the gap between opening 50 and the wafer varies from 0.5 to 6 millimeters. As shown in FIG. 7, detector 58 provides substantially the same intensity of output when the gap distance between the opening 50 and the wafer 42 varies from 0.5 to 6 millimeters. Thus, adequate signals may be obtained even when the wafer is spaced apart from the opening 50 in envelope 48 by a distance of greater than 6 millimeters, such as up to 1 cm. This can be accomplished through optimizing the nozzle and the flow rate. This means that the above-described system has an operation range that spans a wide range of gap distances between the measurement instruments 20 and 100 and the sample that is being measured, so that it will be simple to design a stage 44 for moving the sample and wafer without affecting the measurement system. Since the sample or wafer 42 is not in a vacuum, as opposed to conventional VUV systems, the sample or wafer may be changed at higher speeds compared to conventional VUV systems so as to achieve the high throughput in measuring the sample or wafer. Conventional stages may then also be used for this purpose.

FIG. 7 illustrates the output of detector 58 when a deuterium lamp is employed as source 32. From FIG. 7, it will be observed that, in addition to wavelength components around 0.15 microns (150 nanometers), the deuterium lamp also provides wavelength components at other wavelengths so that the radiation in beams 34 and 40 contain a plurality of wavelength components. Instead of a deuterium lamp, other radiation sources may be employed, such as a flashed xenon radiation source which has a longer life time and provides a very high intensity in VUV radiation but with a low average power of around or less than 20 watts. The repetition rate is in the range of 10-400 Hz. A xenon flash lamp provides radiation with wavelength components covering a wider range of spectrum than deuterium lamps, such as wavelength components ranging from VUV to near infrared. Such a broader spectrum may be desirable for certain applications.

As noted above, optical components 106 and 120 may be polarizers or compensators such as wave plates. One or both components 106 and 120 may be stationary or rotating depending on the amount of information that is desired. Thus, there may be a wide variety of different embodiments that may be constructed from the overall configuration of FIG. 3, depending on whether one or both of the optical components 106, 120 is stationary or rotating and whether they are polarizers or compensators or various combinations. Optical components 106 and 120 may also comprise multiple polarizers and/or compensators. These various combinations are described in more detail in PCT/US00/10875, Publication No. WO 00/65331 filed Apr. 21, 2000, entitled "System for Analyzing Surface Characteristics with Self-Calibrating Capability," which is incorporated by reference in its entirety.

In some of the above-described embodiments, the polarization state of the illumination beam or of the collected radiation 50 is altered in a time-varying manner so that the output of detector 58 would provide more information concerning the reflectivity, film thickness, index of refraction and/or grating parameters of the sample, and/or change of phase of the radiation from source 32 that is caused by the sample. As shown in FIG. 3, the outputs of detector 58 are provided to a device 122 that processes the output to provide information concerning reflectivity, film thickness, index of refraction, grating parameters of the sample and/or change of phase of the radiation caused by the sample. In certain embodiments, device 122 determines information related to one or more ellipsometric parameters of the sample. Such information may then be used for determining the reflectivity, film thickness, index of refraction, grating parameters of the sample, and/or change of phase of the radiation in the beam caused by the sample.

In one embodiment, the broadband radiation provided by source 32 may comprise a range of about 100-1200 nanometers. In other words, the radiation wavelengths of source 32 span VUV, UV, Deep UV ("DUV"), visible and infrared ("IR") ranges. The illumination beam 40 illuminates a spot or area on the surface 42a of the sample, where the area has a dimension not more than about 200 microns. If broadband radiation is desirable in the illumination beam 40 and in the collected radiation 52, it is preferable to employ reflective optics such as objective 110 illustrated in FIGS. 3 and 6. The beams are preferably incident on the reflective surfaces of such reflective optics at high angles of incidence (e.g. less than 30 degrees from the normal incidence direction). The reflective objectives used herein, such as objective 110 and 110' described above and below, comprise preferably spherical mirrored surfaces.

For certain types of applications, it may be desirable to employ an instrument that is simpler and less expensive than spectroscopic ellipsometers that would provide more information concerning the sample than spectroreflectometry. One example of such a system is the polarimeter described in U.S. Pat. No. 6,184,984, which is incorporated herein by reference in its entirety. In such system, a Schwartzschild objective is employed in one embodiment of the system of FIG. 1. Such a configuration is illustrated in FIG. 8. As shown in FIG. 8, a polarized beam 40 is focused by a modified Schwartzschild objective 110' onto area 42a of wafer 42 where the angle of incident can be designed to be have a large angle of incidence. In one embodiment, illumination beam 40 occupies a smaller illumination aperture compared to that shown in FIG. 3B of U.S. Pat. No. 6,184,984. The collected radiation 52 scatters through another portion of the aperture of objective 110' and is collected by the objective and detected by detector 58 (not shown in FIG. 8) and analyzed by device 122 (not shown in FIG. 8) for deriving the reflectivity, film thickness, index of refraction and/or grating parameters of the sample, and/or change of phase of the radiation in the illumination beam caused by the wafer 42.

As shown in FIG. 8, the Schwartzschild objective 110' of FIG. 8 comprises a member 110a and a certain portion 110b connected to member 110a by spiders 110c. Since the beam 40 has an illumination aperture that spins only a portion of the aperture of the objective 110', the illumination beam can be directed to avoid the spiders 110c of FIG. 8.

As noted above, by varying the angle of incidence of the illumination beam 40 and measuring the reflected radiation 52 at such different angles of incidence, more data points may be acquired for determining the reflectivity, film thickness, index of refraction, grating parameters of the sample, and/or change of phase of the radiation in the beam caused by the sample. The use of multiple angles of incidence can help resolve indices of refraction and thicknesses at each wavelength without resorting to the use of dispersion models. Instead of having to perform such measurements sequentially at different angles of incidence, all of these measurements can be performed simultaneously in the multi-angle approach illustrated in FIG. 9.

For simplicity in description, the source 24 of nitrogen gas has been omitted from FIG. 9, it being understood that medium 22 contains nitrogen which is continually or continuously supplied by a nitrogen source not shown in the figure. Preferably, medium 22 is at a higher pressure than the ambient pressure so that the gas medium in medium 22 is continuously being purged through opening 50 so as to reduce the amount of absorbing gas and moisture in the optical paths of the measurement instrument 170 in FIG. 9.

As shown in FIG. 9, system 170 includes a source of polarized laser light 172 where the laser light is focused by an objective 174 to surface 42a of wafer 42 supported on a stage 44 which moves the wafer along X and Y axes or a spiral path (described in more detail below). The refractive objectives used herein, such as lens 174, preferably comprise a suitable material such as calcium fluoride.

The laser light reflected by the wafer 42 is collected by the same objective 174 and is directed to a quarter wave plate 176 which alters the relative phase between the S- and P-polarized components in the collected radiation. The radiation processed by quarter wave plate 176 is then analyzed by analyzer 178 and then detected by the detector 58 which may comprise a detector array. As shown in FIG. 9, the laser light from source 172 is a collimated beam 34' which has a large diameter or cross-sectional dimensions and is focused by objective 174 to a focused beam 40' where different parts of the beam 40' are at different angles of incidence to surface 42a. In this manner, different portions of the reflected beam 52' from surface 42a of the wafer are also at different elevation angles from surface 42a. The collected beam 52' is then collimated by objective 174. Preferably, detector 58 comprises a linear array of detectors where each detector array detects a portion of the collected beam 52', where the detectors in the linear array would detect radiation collected at different elevation angles to surface 42a. In this manner, different detectors in the linear array detect the reflected radiation from different portions of the incident beam 40' that are at different angles of incidence to surface 42a. Hence, radiation reaching the sample at different angles of incidence may be detected simultaneously to reduce the amount of time for measurement. The output of detector 58 is then provided to a device 122 for analysis. Such analysis will yield information concerning characteristics of the sample, such as the reflectivity, film thickness, index of refraction, grating parameters of the sample, and/or change of phase of the radiation in the beam caused by the sample.

While in the embodiment described above, radiation that is reflected by the sample is measured, it will be understood that radiation that is transmitted by the sample may be detected instead in a similar manner to provide the above-described information and characteristics of the sample. Such and other variations are within the scope of the invention.

ANOMALY INSPECTION APPLICATIONS

As noted above, system 20 of FIG. 1 may also be used for inspection applications where anomalies such as particles, pattern defects and surface and subsurface defects of samples are detected, such as those associated with semiconductor wafers. FIG. 10A is a perspective view of an inspection system 200 in such an application. System 200 is described in more detail in U.S. Pat. No. 5,883,710 which is incorporated herein by reference in its entirety. As shown in FIG. 10A, source 32 provides a radiation beam 34 which is expanded by a beam expander 202 and passed to an acousto-optic deflector 204 and a lens system 206 which focuses the focused beam 40 to a spot on the surface 42a of a semiconductor wafer 42 that is supported by stage 44. Stage 44 moves the wafer along the X and Y axes so that the illuminated spot scans a serpentine path on the surface of the wafer 42. The surface of the wafer may be unpatterned as illustrated at 218 or patterned as illustrated at 219. Radiation scattered by the surface and any anomalies within the illuminated spot on the surface 42a of wafer 42 is detected by means of at least four detectors: 210a, 210b, 211a and 211b. This specular reflection of beam 40 is detected by a bright field detector 240.

FIG. 10B is a schematic view of a portion of system 200 of FIG. 10A to illustrate one embodiment of the invention. As shown in FIG. 10B, the incident illumination beam 40 passes through opening 50 of the enclosure 48 to illuminate a spot on area 42a of wafer 42. The radiation or light scattered by the surface at 42a and any anomalies associated therewith pass back through the opening 50 and are detected by detectors (not shown in FIG. 10B). Preferably, the optical components described above and below for illuminating surface 42a and for collecting and detecting the scattered light or radiation are placed within enclosure 48; these components as well as nitrogen source 24 are omitted from FIG. 10B to simplify the drawing. As shown in FIG. 10B, wafer 42 and stage 44 are placed outside the enclosure 48 so that the wafer can be moved freely and unconstrained by the enclosure to ensure adequate throughput for in-line inspection.

The acousto-optical deflector 204 causes the illuminated spot to scan along a scan line along the X axis. After the illuminated spot has covered such scan line, wafer 42 is moved by a small distance along the Y axis so that the acousto-optic deflector may cause beam 40 to scan another scan line adjacent to the one previously scanned. This process may be repeated until the illuminated spot has covered a strip area on the wafer surface, and wafer 42 is then moved along the Y direction by about the length of the scan line so that another strip area of the wafer may be scanned in a similar fashion.

FIG. 10C is a top schematic view illustrating the illumination and collection angles of system 100 of FIG. 10A. As shown in FIG. 10C, the solid collection angles of collection channels 210a, 210b are labeled $\Phi_1$ and those of collection channels 211a, 211b are labeled $\Phi_2$. The azimuthal angles of collection of the different collectors are defined by the angle that the collection path makes with the plane of incidence of the illumination beam 40. The plane of incidence of beam 40 is defined as the plane that contains the beam and the line that is normal to surface of the wafer 42 passing through beam 40. In reference to FIG. 10A, line 250 is normal to the surface of wafer 42 and passes through beam 40. Therefore, the azimuthal collection angles of detectors 210a and 210b are both centered at ±90° azimuthal angles (defining double dark field collection and detection) and has a solid collection angle of about 30° each. In contrast, the detectors 211a and 211b collect radiation centered at ±45° azimuthal angles and has a solid angle of collection of 30° each. Collectors or detectors that collect or detect radiation scattered away from the specular reflection direction of the illumination beam are referred to as dark field collectors or detectors. Thus all four detectors 210a, 210b, 211a, 211b (and detection channel 221) are dark field detectors. In addition to these four detectors, system 200 also includes an imaging detection channel 221 that is directly above wafer 42 to detect radiation scattered at or near the normal direction 250 and an alignment/registration detection channel 222. The output of all of the above-described detectors are then provided to a processing device 122 such as a microprocessor that is preferably placed outside the enclosure 48 (not shown in FIG. 10A).

In the embodiment of FIG. 11, a sample surface is scanned with oblique and normal illumination beams. FIG. 11 is a schematic view of a sample inspection system 300 to illustrate a general set up for implementing anomaly detection using both normal and oblique illumination beams. A radiation source 32 that provides radiation at one or more wavelengths in a wide electromagnetic spectrum (including but not limited to ultraviolet, visible, infrared) may be used, such as a laser 32 providing a laser beam 34. A lens 302 focuses the beam 34 through a spatial filter 304 and lens 306 collimates the beam and conveys it to a polarizing beamsplitter 308. Beamsplitter 308 passes a first polarized component to the normal illumination channel and a second polarized component to the oblique illumination channel, where the first and second components are orthogonal. In the normal illumination channel 310, the first polarized component is focused by optics 312 and reflected by mirror 314 towards a sample surface 42a of a semiconductor wafer 42. The radiation scattered by surface 42a is collected and focused by an ellipsoidal mirror 316 to a photomultiplier tube 320 through an analyzer 318.

In the oblique illumination channel 330, the second polarized component is reflected by beamsplitter 308 to a mirror 332 which reflects such beam through a halfwave plate 334 and focused by optics 336 to surface 42a. Radiation originating from the oblique illumination beam in the oblique channel 330 and scattered by surface 42a is collected by an ellipsoidal mirror 316 and focused to photomultiplier tube 320. Photomultiplier tube 320 has a pinhole entrance 320a. The pinhole 320a and the illuminated spot (from the normal and oblique illumination channels on surface 42a) are preferably at the foci of the ellipsoidal mirror 316. Spatial filter 390 may be employed to selectively block scattered radiation within one or more ranges of azimuthal collection angles from reaching the PMT 320 to simulate any arrangement of collection such as double dark field collection and detection.

Wafer 42 is rotated by a motor 392 which is also moved linearly by a transducer 394, and both movements are controlled by a controller 396 under the overall control of device 122 (control lines not shown), so that the normal and oblique illumination beams in channels 310 and 330 scan surface 42a along a spiral scan path to cover the entire surface.

Instead of using an ellipsoidal mirror to collect the light scattered by surface 42a, it is also possible to use other curved mirrors, such as a paraboloidal mirror. The paraboloidal mirror collimates the scattered radiation from surface 42a into a collimated beam and the collimated beam is then focused by an objective and through an analyzer 318 to the photomultiplier tube 320. Curved mirrored surfaces having shapes other than paraboloidal or ellipsoidal shapes may also be used; preferably, each of such curved mirrored surfaces has an axis of symmetry substantially coaxial with the path of the normal illumination path, and defines an input aperture for receiving scattered radiation. All such variations are within the scope of the invention. Device 122 analyzes the output of PMT 320 to determine the presence and classification of anomalies associated with the surface 42a or wafer 42.

FIGS. 12A, 12B are schematic views illustrating yet another arrangement of detectors different from that of FIG. 11 to illustrate another embodiment of the invention. In reference to FIG. 11, it will be noted that since the ellipsoidal or paraboloidal mirror 316 is rotationally symmetrical about a line normal to the surface 42a, such mirror preserves the directional information of the scattered radiation it collects, so that by appropriately designing filter 390, radiation scattered within certain predetermined ranges of azimuthal angles may be blocked to simulate any arrangement of collection in the ranges of azimuthal angles in which radiation is collected, such as the double dark field collection and detection arrangement.

Instead of using the combination of a spatial filter and a collector such as ellipsoidal or paraboloidal mirror as in FIG. 11, individual collectors and/or detectors may be employed for detecting radiation scattered in the different ranges of azimuthal angles in an arrangement such as illustrated in FIG. 12A. For simplicity in description, the illumination beams and the wafer have been omitted in FIG. 12A to simplify the figure, it is understood that two or more illumination beams may be employed at different angles of incidence, including normal incidence. The two or more illumination beams may be employed, either simultaneously or sequentially, to illuminate the wafer just underneath the opening 50 of the enclosure 48.

FIG. 12A is a view from the top of the enclosure and the wafer along a direction normal to the wafer. As shown in FIG. 12A, a total of 16 detectors 58(1) through 58(16) are employed, each detecting radiation scattered within a solid angle centered at one of 16 different azimuthal angles distributed evenly around a normal direction 402. The outputs of the 16 detectors are then provided to a processing device such as device 122 (not shown in FIG. 12A) for analysis and a determination of anomalies associated with the surface of the wafer. Instead of employing detectors to directly receive the scattered radiation within a particular range of azimuthal angles of scattering, it may also be possible to employ 16 individual collectors to collect such radiation and then each collector conveys the collected radiation to a corresponding detector. In one embodiment, such collectors may comprise optical fibers.

In addition to detecting individually radiation scattered within different ranges of azimuthal angles, it is also possible to detect separately and individually radiation scattered by the wafer at different elevation angles as illustrated in FIG. 12B. As shown in FIG. 12B (source of nitrogen has been omitted to simplify the figure), the surface of the wafer 42 is illuminated by two illumination beams in directions oblique and normal to the surface of the wafer by means of radiation sources 452 and 454, respectively. Obviously, the surface of the wafer may be illuminated at other angles as well, such as at two different oblique angles to the surface of the wafer. Also, more than two illumination beams may be employed. Such and other variations are within the scope of the invention.

As shown in FIG. 12B, radiation from the illumination beams scattered by the wafer 42 is collected by two different sets of detectors 462 and 464 that are arranged to collect and detect radiation scattered at different elevation angles from the surface of the wafer. Each set of detectors 462 and 464 may comprise a number of detectors, distributed preferably evenly around the normal direction 402 similar to the distribution of detectors 58(1)-58(16) as shown in FIG. 12A. While two sets of collectors 462, 464 are shown in FIG. 12B to collect at two different elevation angles, it will be understood that fewer or more sets of detectors may be employed and are within the scope of the invention. As in FIG. 12A, instead of employing detectors to collect and detect radiation scattered at different angles, collectors such as optical fibers may be employed to first collect the scattered radiation and then convey the collected radiation to detectors so that the radiation collected by each individual collector is detected by a separate detector.

FIG. 13 is a schematic view of an anomaly detection system 500 to illustrate yet another embodiment of the invention. As shown in FIG. 13, system 500 includes a radiation source 32 which provides a radiation beam 34 and a beam expander 202 which expands the beam 34. The expanded beam is reflected by mirror 502 to an acousto-optic deflector 204 and focused by lenses 206 to the surface 42a of the wafer 42. Reflection of the beam 40 off of the surface of the wafer is collected by an objective 512 and detected by a bright field detector 510. The radiation from beam 40 that is scattered by the wafer is collected by three different collectors: a forward channel collector 521 collecting radiation scattered forwardly from wafer 42, a center channel collector 523 collecting radiation scattered in directions substantially normal to the surface of the wafer, and a back channel collector 525 collecting radiation scattered backwardly from the surface of the wafer. Radiation collected by collector 521 is conveyed to a corresponding detector 522. Where the collector 521 is an objective, the objective focuses the collected radiation to detector 522. Similarly, radiation collected by collector 523 is conveyed optically to detector 524, and the radiation collected by collector 525 is conveyed optically to detector 526. The outputs of detectors 510, 522, 524 and 526 are supplied through wires or cables to the signal discrimination circuitry 550 (which may be a processor) for analysis and determination on the presence of classification of anomalies associated with the wafer. The wafer is supported by a stage 44 which is moved so that beam 40 scans a spiral path on the surface of the wafer in the same manner as that described above in reference to FIG. 11.

The radiation sources in all of the embodiments described herein provide at least one VUV wavelength, component. In all of the embodiments, the optical components in the illuminating paths and collection and detection paths are preferably enclosed within enclosures where preferably at least some of the ambient gas(es) and moisture have been displaced by a gas that does not substantially absorb VUV radiation.

FIG. 14 is a schematic view of a measurement system 600 for measuring characteristics of a sample to illustrate another embodiment of the invention where laminar flow of gas from the envelope is enhanced compared to certain other embodiments. As shown in FIG. 14, system 600 includes a source 24 of purge gas such as nitrogen, and gas lines 602a and 602b. Envelope 48 houses an optical instrument 20 for measuring the metrology of samples or for inspecting anomalies of samples, such as in any one of the above-described embodiments. Envelope 48 also contains a sub-chamber, preferably in the shape of a ring manifold 48a, which is separate and apart from the main chamber 22 within envelope 48 for housing system 20. Gas line 602a supplies the purge gas to the main chamber 22 within envelope 48. Gas line 602b supplies the purge gas to the ring manifold 48a.

The purge gas that is supplied to the ring manifold 48a then escapes through orifices 604, where the orifices are located in envelope 48 so that they face the wafer 42 and are adjacent to opening 50 through which the illumination and detection paths 40 and 52 pass between system 20 and wafer 42. The gas that is supplied to the ring manifold 48a then flows through a space 606 that is between the wafer and envelope 48 but in radial directions flowing away from opening 50, forming a sheet-like radial second gas flow 607 outwards through space 606 and away from space 50. This would have the effect of shielding the region containing and surrounding opening 50 from an atmosphere 608 surrounding the envelope 48. This reduces the chances of oxygen and moisture in the atmosphere 608 from entering into such region and into opening 50 to interfere with the optical measurements described above. The ring manifold 48a is maintained at a higher pressure than atmosphere 608 to ensure flow 607 is directed out of manifold 48a and not into it. Chamber 22 needs to be maintained at a higher pressure than both atmosphere 608 and the pressure of the ring manifold 48a to ensure that the flow 50 is directed out of chamber 22 and not into it. A small pressure differential between chamber 22 and manifold 48a may be adequate. When the pressure differential between chamber 22 and that of manifold 48a is at a lower level than otherwise possible without the second flow 607, laminar flow through opening 50 would be enhanced and turbulence at the opening would be reduced, compared to the situation where the radial flow 607 is not present. The supply of gas through lines 602a, 602b to chamber 22 and manifold 48a may be controlled by flow controllers 612.

FIG. 15 is a schematic view of a measurement system for measuring characteristics of the sample to illustrate a further embodiment of the invention where laminar flow is enhanced. Instead of shielding the region containing opening 50 by means of a second gas flow as in the embodiment of FIG. 14, similar effects can be achieved by means of an obstruction placed within the space 606 as illustrated in FIG. 15. As shown in FIG. 15, a preferably ring-shaped obstruction 620 surrounding opening 50 is placed in the space 606. Thus, the gases escaping from chamber 22 into space 606 must pass through a restricted exit 622 between the obstruction, envelope 48 and wafer 42. Since the clearance between these three members would be small, the gas flow through this exit would be fast and turbulent across this clearance. The clearance between the envelope 48 and the wafer at the opening 50, however, is much larger in comparison so that the gas flow through opening 50 is slow and laminar.

The obstruction 620 again reduces the chances that oxygen and moisture from the atmosphere 608 would enter a region where opening 50 is located. Preferably, obstruction 620 may be a ring attached to the surface of envelope 48 facing wafer 42. The embodiment of FIG. 15 has the advantage of not requiring another gas flow controller and a manifold in the envelope 48, which simplifies the design. In the embodiment of FIG. 15, however, it may be desirable to slightly increase the separation between envelope 48 and the wafer.

While the invention has been described above by reference to various embodiments, it will be understood that changes and modifications may be made without departing from the scope of the invention, which is to be defined only by the appended claims and their equivalents. All references referred to herein are incorporated herein by reference in their entireties.

What is claimed is:

1. An optical method for measuring characteristics of a sample, comprising:

illuminating a surface of the sample by a beam of radiation along an illumination path, radiation in said beam comprising at least one wavelength component in a vacuum ultraviolet (VUV) range;

detecting radiation from the surface originating from the beam along a detection path to provide at least one output signal;

reducing amount of ambient absorbing gases and moisture present in at least a portion of each of the illumination and detection paths without employing a vacuum chamber, by displacing said gases and moisture with another gas that does not substantially absorb the at least one VUV wavelength component so as to reduce attenuation of the at least one VUV wavelength component, wherein the reducing includes supplying said another gas from a direction transverse to a direction normal to the surface of the sample and to at least one of the illumination and detection paths; and determining the characteristics of the surface from said at least one output signal.

2. The method of claim 1, wherein said determining determines information related to metrology of the sample.

3. The method of claim 2, wherein said information is related to reflectivity, film thickness, index of refraction, and/or grating parameters of the sample.

4. The method of claim 3, wherein said grating parameters of the sample comprise critical dimension, wall angle, pitch, height and/or profile of gratings.

5. The method of claim 1, wherein radiation in the beam is polarized.

6. The method of claim 5, further comprising causing polarization of detected radiation from the beam to vary with time.

7. The method of claim 6, said causing comprising rotating a polarizer or compensator in the illumination and/or detection paths.

8. The method of claim 6, wherein said information is related to reflectivity, film thickness, index of refraction, and/or grating parameters of the sample, and/or change of phase of the radiation in the beam caused by the sample.

9. The method of claim 6, wherein said rotating rotates a polarizer, said method further comprising comparing phase shifts caused by the sample in the output signal to two orthogonally polarized radiation components in the detected radiation to find a reference for measurement.

10. The method of claim 1, wherein said determining determines information related to an ellipsometric parameter of the sample.

11. The method of claim 10, wherein said illuminating comprises selecting an angle of incidence of the beam at a surface of the sample to increase sensitivity of detection of said ellipsometric parameter.

12. The method of claim 11, wherein said sample comprises a silicon nitride layer, and said selecting selects an angle of incidence of the beam at a surface of the sample to increase sensitivity of detection of said ellipsometric parameter of said silicon nitride layer.

13. The method of claim 10, wherein said information is related to reflectivity, film thickness, index of refraction, and/or grating parameters of the sample, and/or change of phase of the radiation in the beam caused by the sample.

14. The method of claim 1, wherein said illuminating comprises varying an angle of incidence of the beam at a surface of the sample and said detecting detects radiation from the surface at a corresponding angle.

15. The method of claim 14, wherein said information is related to reflectivity, film thickness, index of refraction, and/or grating parameters of the sample, and/or change of phase of the radiation in the beam caused by the sample.

16. The method of claim 1, wherein said illuminating comprises illuminating the surface at different angles of incidence substantially simultaneously and said detecting detects radiation from the surface along detection paths at different elevation angles from the surface substantially simultaneously.

17. The method of claim 16, wherein said information is related to reflectivity, film thickness, index of refraction, and/or grating parameters of the sample, and/or change of phase of the radiation in the beam caused by the sample.

18. The method of claim 1, wherein said illuminating comprises illuminating the surface at different azimuthal angles substantially simultaneously and said detecting detects radiation from the surface along detection paths at different azimuthal angles from the surface substantially simultaneously.

19. The method of claim 18, wherein said information is related to reflectivity, film thickness, index of refraction, and/or grating parameters of the sample, and/or change of phase of the radiation in the beam caused by the sample.

20. The method of claim 1, wherein said illuminating comprises illuminating the surface with radiation of multiple wavelength components and said detecting detects ellipsometric parameters of the sample.

21. The method of claim 20, wherein said information is related to reflectivity, film thickness, index of refraction, and/or grating parameters of the sample, and/or change of phase of the radiation in the beam caused by the sample.

22. The method of claim 20, wherein said multiple wavelengths are in the visible, UV, DUV, VUV and/or IR ranges.

23. The method of claim 20, wherein said multiple wavelength components comprise broadband radiation.

24. The method of claim 1, wherein said illuminating comprises focusing the beam to an area on a surface of the sample, said area having a dimension not more than about 200 microns.

25. The method of claim 1, wherein said illuminating comprises supplying broadband radiation to illuminate the sample.

26. The method of claim 25, wherein said broadband radiation comprises wavelength components in a range of about 100 to 1200 nm.

27. The method of claim 1, wherein said determining determines information related to anomalies on or near a surface of the sample.

28. The method of claim 27, wherein said detecting detects radiation in a bright field, dark field and/or double dark field arrangement.

29. The method of claim 27, further comprising causing the surface to be scanned by a beam of radiation.

30. The method of claim 27, further comprising causing the surface to be scanned by a beam of radiation when radiation from the beam is detected to determine information related to anomalies on or near an area of the surface of the sample.

31. The method of claim 30, wherein said causing causes the beam to scan a serpentine or spiral path on the surface.

32. The method of claim 30, wherein said causing causes the surface to be moved without moving the illumination and detection paths.

33. The method of claim 27, wherein said detecting detects, separately and by means of different detection channels, radiation from the beam scattered by the surface in different directions that are arranged substantially symmetrically about a line normal to the surface.

34. The method of claim 27, wherein said beam is at an oblique angle to the surface of the sample, and wherein said detecting detects, separately and by means of different detection channels, radiation from the beam scattered by the surface within different ranges of azimuthal angles relative to the beam.

35. The method of claim 27, further comprising collecting radiation from the beam and scattered in different directions from the surface by means of a collector that is substantially symmetrical about a line normal to the surface.

36. The method of claim 27, wherein said detecting detects, separately and by means of different detection channels, radiation from the beam scattered by the surface in different directions that are at different elevation angles from the surface.

37. The method of claim 27, wherein said detecting detects separately two or more of the following: forward scattered radiation, back scattered radiation and radiation scattered in a direction normal to the surface.

38. The method of claim 27, wherein said illuminating comprises directing said beam at a normal direction to the surface of the sample.

39. The method of claim 27, wherein said illuminating comprises directing said beam at an oblique direction to the surface of the sample.

40. The method of claim 1, wherein said reducing comprises directing a stream of gas to said at least a portion of each of the illumination and detection paths.

41. The method of claim 40, wherein said directing directs the stream of gas from a source of the gas that contains substantially no absorbing gas and moisture.

42. The method of claim 41, wherein said directing directs the stream of gas from a source of nitrogen or an inert gas.

43. The method of claim 40, wherein said directing directs the stream of gas towards a measurement area on the surface illuminated by the beam.

44. The method of claim 43, wherein said directing is such that laminar flow of the gas at or near the measurement area is enhanced.

45. The method of claim 43, wherein said directing is such that at least some contaminants and moisture at or near the measurement area on the surface are removed.

46. The method of claim 43, wherein said directing is such that turbulent flow of the gas at or near the measurement area is reduced.

47. The method of claim 1, wherein said reducing comprises enclosing in an envelope of at least a portion of each of the illumination and detection paths in a gas that contains less oxygen and moisture than those in an atmosphere surrounding said envelope.

48. The method of claim 47, wherein said illuminating illuminates a measurement area on the surface, said method further comprising maintaining said envelope at a pressure higher than that at a portion of each of the illumination and detection paths outside the envelope and near the measurement area on the surface.

49. The method of claim 47, wherein said illuminating illuminates a measurement area on the surface, said envelope defining an opening, the illumination and detection paths passing through the opening, said reducing further comprising directing a stream of gas from the envelope through the opening towards the measurement area on the surface.

50. The method of claim 49, further comprising causing the opening to be within 1 cm from the surface.

51. The method of claim 47, wherein said sample is outside of the envelope during the illuminating, collecting, reducing and detecting.

52. The method of claim 1, wherein said illuminating employs illumination optics, said detecting employs detection optics and said reducing includes substantially sealing an envelope containing at least part of said illumination and detection optics.

53. A optical apparatus for measuring characteristics of a sample, comprising:
   optics illuminating a surface of the sample by a beam of radiation along an illumination path, radiation in said beam comprising at least one wavelength component in a vacuum ultraviolet range;
   a detector detecting radiation from the surface originating from the beam along a detection path to provide at least one output signal;
   an instrument reducing amount of ambient absorbing gases and moisture present in at least a portion of each of the illumination and detection paths without employing a vacuum chamber, by displacing said gases and moisture with another different gas so as to reduce attenuation of the at least one wavelength component, wherein the instrument supplies said another gas from a direction transverse to a direction normal to the surface of the sample and to at least one of the illumination and detection paths; and
   means for determining the characteristics of the surface from said at least one output signal.

54. The apparatus of claim 53, wherein said determining means determines information related to metrology of the sample.

55. The apparatus of claim 54, wherein said information is related to reflectivity, film thickness, index of refraction, and/or grating parameters of the sample, and/or change of phase of the radiation in the beam caused by the sample.

56. The apparatus of claim 55, wherein said grating parameters of the sample comprise critical dimension, wall angle, pitch, height and/or profile of gratings.

57. The apparatus of claim 54, wherein said information is related to reflectivity, film thickness, index of refraction, and/or grating parameters of the sample, and/or change of phase of the radiation in the beam caused by the sample.

58. The apparatus of claim 53, wherein radiation in the beam is polarized.

59. The apparatus of claim 58, further comprising a device rotating a polarizer or compensator in the illumination and/or detection paths.

60. The apparatus of claim 59, wherein said information is related to reflectivity, film thickness, index of refraction, and/or grating parameters of the sample, and/or change of phase of the radiation in the beam caused by the sample.

61. The apparatus of claim 59, wherein said device rotates a polarizer, said determining means comparing phase shifts caused by the sample in the output signal to two orthogonally polarized radiation components in the detected radiation to find a reference for measurement.

62. The apparatus of claim 53, wherein said determining means determines information related to an ellipsometric parameter of the sample.

63. The apparatus of claim 61, wherein said optics comprises a device selecting an angle of incidence of the beam at the surface of the sample to increase sensitivity of detection of said ellipsometric parameter.

64. The apparatus of claim 63, wherein said sample comprises a silicon nitride layer, and said device selects an angle of incidence of the beam at the surface of the sample to increase sensitivity of detection of said ellipsometric parameter of said silicon nitride layer.

65. The apparatus of claim 62, wherein said information is related to reflectivity, film thickness, index of refraction, and/or grating parameters of the sample, and/or change of phase of the radiation in the beam caused by the sample.

66. The apparatus of claim 53, wherein said optics varies an angle of incidence of the beam at a surface of the sample and said detector detects radiation from the surface at a corresponding angle.

67. The apparatus of claim 66, wherein said information is related to reflectivity, film thickness, index of refraction, and/or grating parameters of the sample, and/or change of phase of the radiation in the beam caused by the sample.

68. The apparatus of claim 53, said optics illuminating the surface at different angles of incidence substantially simultaneously and said detector detects radiation from the surface along detection paths at different elevation angles from the surface substantially simultaneously.

69. The apparatus of claim 68, wherein said information is related to reflectivity, film thickness, index of refraction, and/or grating parameters of the sample, and/or change of phase of the radiation in the beam caused by the sample.

70. The apparatus of claim 53, said optics illuminating the surface at different azimuthal angles substantially simultaneously and said detector detects radiation from the surface along detection paths at different azimuthal angles from the surface substantially simultaneously.

71. The apparatus of claim 70, wherein said information is related to reflectivity, film thickness, index of refraction, and/or grating parameters of the sample, and/or change of phase of the radiation in the beam caused by the sample.

72. The apparatus of claim 53, said optics illuminating the surface with radiation of multiple wavelength components and the detector detects ellipsometric parameters of the sample.

73. The apparatus of claim 72, wherein said multiple wavelengths are in the visible, UV, DUV, VUV and/or IR ranges.

74. The apparatus of claim 72, wherein said multiple wavelength components comprise broadband radiation.

75. The apparatus of claim 53, wherein said optics comprises an objective focusing the beam to an area on the surface of the sample, said area having a dimension not more than about 200 microns.

76. The apparatus of claim 53, said optics supplying broadband radiation to illuminate the sample.

77. The apparatus of claim 76, wherein said broadband radiation comprises wavelength components in a range of about 100 to 1200 nm.

78. The apparatus of claim 53, wherein said determining means determines information related to anomalies on or near the surface of the sample.

79. The apparatus of claim 78, wherein said detector detects radiation in a bright field, dark field and/or double dark field arrangement.

80. The apparatus of claim 78, further comprising a device causing the surface to be scanned by a beam of radiation.

81. The apparatus of claim 78, said device causing the surface to be scanned by a beam of radiation when radiation from the beam is detected to determine information related to anomalies on or near an area of the surface of the sample.

82. The apparatus of claim 81, wherein said device causes the beam to scan a serpentine or spiral path on the surface.

83. The apparatus of claim 81, wherein said device causes the surface to be moved without moving the optics and detector.

84. The apparatus of claim 78, wherein said detector comprises different detection channels, said detector comprising a plurality of detection channels detecting separately radiation from the beam scattered by the surface in different directions that are substantially symmetrically about a line normal to the surface.

85. The apparatus of claim 78, wherein said beam is at an oblique angle to the surface of the sample, said detector comprising a plurality of detection channels detecting separately radiation from the beam scattered by the surface within different ranges of azimuthal angles relative to the beam.

86. The apparatus of claim 78, further comprising a collector that is substantially symmetrical about a line normal to the surface collecting radiation from the beam and scattered in different directions from the surface, wherein the detector detects the radiation that is collected by the detector.

87. The apparatus of claim 78, wherein said detector comprises different detection channels, said detector comprising a plurality of detection channels detecting separately radiation from the beam scattered by the surface in different directions that are at different elevation angles from the surface.

88. The apparatus of claim 78, said detector comprising a plurality of detection channels detecting separately two or more of the following: forward scattered radiation, back scattered radiation and radiation scattered in a direction normal to the surface.

89. The apparatus of claim 78, said optics directing said beam at a normal direction to the surface of the sample.

90. The apparatus of claim 78, said optics directing said beam at an oblique direction to the surface of the sample.

91. The apparatus of claim 53, said instrument directing a stream of gas to said at least a portion of each of the illumination and detection paths.

92. The apparatus of claim 91, wherein said instrument directs the stream of gas from a source of the gas that contains substantially no absorbing gas and moisture.

93. The apparatus of claim 92, wherein said instrument directs the stream of gas from a source of nitrogen or an inert gas.

94. The apparatus of claim 91, wherein said instrument directs the stream of gas towards a measurement area on the surface illuminated by the beam.

95. The apparatus of claim 94, wherein said instrument causes laminar flow of the gas at or near the measurement area to be enhanced.

96. The apparatus of claim 94, wherein said instrument directs the gas towards the measurement area such that at least some contaminants and moisture at or near the measurement area on the surface are removed.

97. The apparatus of claim 94, wherein said instrument causes turbulent flow of the gas at or near the measurement area to be reduced.

98. The apparatus of claim 53, wherein said instrument comprises an envelope enclosing therein of at least a portion of each of the illumination and detection paths in a gas that contains less oxygen and moisture than those in an atmosphere surrounding said envelope.

99. The apparatus of claim 98, wherein said illuminating illuminates a measurement area on the surface, and wherein said envelope is at a pressure higher than that at a portion of each of the illumination and detection paths outside the envelope and near the measurement area on the surface.

100. The apparatus of claim 98, wherein said illuminating illuminates a measurement area on the surface, said envelope defining a hole therein, the illumination and detection paths passing through the hole, said instrument directing a stream of gas from the envelope through the hole towards the measurement area on the surface.

101. The apparatus of claim 100, the hole being within 1 cm from the surface.

102. The apparatus of claim 100, the hole having a tapered or funnel shape.

103. The apparatus of claim 102, the hole having a first and a second end where the first end is closer to the surface and is smaller than the second end.

104. The apparatus of claim 102, further comprising an objective in the envelope adjacent to the hole for focusing radiation in the illumination and detection paths.

105. The apparatus of claim 100, the hole having two ends that are larger than a section of the hole between the two ends.

106. The apparatus of claim 100, the hole having two ends wherein the hole has substantially the same dimension between the two ends.

107. The apparatus of claim 106, further comprising a tube shaped member in the envelope adjacent to the hole.

108. The apparatus of claim 100, wherein the hole is elongated in shape to accommodate illumination by the beam at an oblique angle to the surface.

109. The apparatus of claim 108, wherein the hole is substantially elliptical in shape.

110. The apparatus of claim 98, wherein said sample is outside of the envelope.

111. The apparatus of claim 53, wherein said optics comprises reflective optics.

112. The apparatus of claim 111, wherein said optics comprises at least one substantially spherical mirrored surface.

113. The apparatus of claim 53, wherein said optics comprises at least one lens comprising calcium fluoride.

114. The apparatus of claim 53, further comprising a collector that is collecting radiation from the beam and scattered by the surface, wherein the detector detects the radiation that is collected by the detector.

115. The apparatus of claim 114, wherein said collector comprises reflective optics.

116. The apparatus of claim 115, wherein said collector comprises at least one substantially paraboloidal or ellipsoidal mirrored surface.

117. The apparatus of claim 115, wherein said collector comprises at least one substantially ellipsoidal mirrored surface that has an axis that is substantially normal to the surface.

118. The apparatus of claim 114, wherein said collector comprises a plurality of collection devices arranged in a ring surrounding a portion of the surface illuminated by the beam.

119. The apparatus of claim 114, wherein said collector comprises at least one lens comprising calcium fluoride.

120. The apparatus of claim 53, said instrument comprising a substantially sealed envelope containing at least part of said illumination path and at least part of said detection illumination path.

121. An optical apparatus for measuring characteristics of a sample, comprising:
optics illuminating a surface of the sample by a beam of radiation along an illumination path, radiation in said beam comprising at least one wavelength component in a vacuum ultraviolet range;
a detector detecting radiation from the surface originating from the beam along a detection path to provide at least one output signal;
an instrument reducing amount of ambient absorbing gases and moisture present in at least a portion of each of the illumination and detection paths by displacing said gases and moisture with another different gas so as to reduce attenuation of the at least one wavelength component, said instrument comprising an envelope having an opening and enclosing said optics and detector and containing a gas that contains less oxygen and moisture than those in an atmosphere surrounding said envelope and that is at a higher pressure than said atmosphere, wherein said amount is reduced by a flow of said different gas in the envelope and said opening;
means for shielding the opening from the atmosphere to enhance laminar flow of the gas through the opening; and
means for determining the characteristics of the surface from said at least one output signal.

122. The apparatus of claim 121, wherein said shielding means comprises a gas that does not absorb the at least one VUV wavelength component flowing through a space between the sample and the envelope away from the opening.

123. The apparatus of claim 121, wherein said shielding means comprises an obstruction between the sample and the envelope.

124. The apparatus of claim 123, wherein said obstruction is adjacent to or in contact with an outside surface of the envelope.

125. An optical method for measuring characteristics of a sample, comprising:
illuminating a surface of the sample by a beam of radiation along an illumination path, radiation in said beam comprising at least one wavelength component in a vacuum ultraviolet (VUV) range;
detecting radiation from the surface originating from the beam along a detection path to provide at least one output signal;
maintaining within an envelope pressure of a gas so that it is higher than that of an atmosphere surrounding said envelope, said envelope enclosing at least a portion of each of the illumination and detection paths, said gas containing less oxygen and moisture than the atmosphere, so that said gas escapes through an opening of the envelope;
shielding the opening from the atmosphere to enhance laminar flow of the gas through the opening and to reduce amount of ambient absorbing gases and moisture present in at least a portion of each of the illumination and detection paths; and
determining the characteristics of the surface from said at least one output signal.

126. The method of claim 125, wherein said shielding comprises causing a gas that does not absorb the at least one VUV wavelength component to flow through a space between the sample and the envelope away from the opening.

127. The apparatus of claim 125, wherein said shielding comprises obstructing a space between the sample and the envelope.

128. An optical method for measuring characteristics of a sample, comprising:
illuminating a surface of the sample by a beam of radiation along an illumination path, radiation in said beam comprising at least one wavelength component in a vacuum ultraviolet (VUV) range;
detecting radiation from the surface originating from the beam along a detection path to provide at least one output signal;
reducing amount of ambient absorbing gases and moisture present in at least a portion of each of the illumination and detection paths without placing the sample in a vacuum, by displacing said gases and moisture with at least another gas that does not substantially absorb the at least one VUV wavelength component so as to reduce attenuation of the at least one VUV wavelength component, wherein the reducing includes supplying said at least another gas along two different paths to the surface of the sample; and determining the characteristics of the surface from said at least one output signal.

129. The method of claim 128, wherein said determining determines information related to metrology of the sample.

130. The method of claim 129, wherein said information is related to reflectivity, film thickness, index of refraction, and/or grating parameters of the sample.

131. The method of claim 130, wherein said grating parameters of the sample comprise critical dimension, wall angle, pitch, height and/or profile of gratings.

132. The method of claim 128, wherein radiation in the beam is polarized.

133. The method of claim 132, further comprising causing polarization of detected radiation from the beam to vary with time.

134. The method of claim 133, said causing comprising rotating a polarizer or compensator in the illumination and/or detection paths.

135. The method of claim 128, wherein said illuminating comprises varying an angle of incidence of the beam at a surface of the sample and said detecting detects radiation from the surface at a corresponding angle.

136. The method of claim 128, wherein said illuminating comprises illuminating the surface at different angles of incidence substantially simultaneously and said detecting detects radiation from the surface along detection paths at different elevation angles from the surface substantially simultaneously.

137. The method of claim 128, wherein said illuminating comprises illuminating the surface at different azimuthal angles substantially simultaneously and said detecting detects radiation from the surface along detection paths at different azimuthal angles from the surface substantially simultaneously.

138. The method of claim 128, wherein said illuminating comprises illuminating the surface with radiation of multiple wavelength components and said detecting detects ellipsometric parameters of the sample.

139. The method of claim 138, wherein said multiple wavelengths are in the visible, UV, DUV, VUV and/or IR ranges.

140. The method of claim 128, wherein said illuminating comprises focusing the beam to an area on a surface of the sample, said area having a dimension not more than about 200 microns.

141. The method of claim 128, wherein said determining determines information related to anomalies on or near a surface of the sample.

142. The method of claim 141, wherein said detecting detects radiation in a bright field, dark field and/or double dark field arrangement.

143. The method of claim 128, wherein said reducing comprises enclosing in an envelope of at least a portion of each of the illumination and detection paths in a gas that contains less oxygen and moisture than those in an atmosphere surrounding said envelope, and wherein said illuminating illuminates a measurement area on the surface, said method further comprising maintaining said envelope at a pressure higher than that at a portion of each of the illumination and detection paths outside the envelope and near the measurement area on the surface.

144. The method of claim 143, said envelope defining an opening, the illumination and detection paths passing through the opening, said reducing further comprising directing a stream of gas from the envelope through the opening towards the measurement area on the surface, further comprising causing the opening to be within 1 cm from the surface.

145. The method of claim 128, wherein said at least another different gas is supplied along a first path through an opening, and along second paths through orifices in a sheet-like radial flow away from the opening to the surface of the sample.

146. A optical apparatus for measuring characteristics of a sample, comprising:
  optics illuminating a surface of the sample by a beam of radiation along an illumination path, radiation in said beam comprising at least one wavelength component in a vacuum ultraviolet range;
  a detector detecting radiation from the surface originating from the beam along a detection path to provide at least one output signal;
  an instrument reducing amount of ambient absorbing gases and moisture present in at least a portion of each of the illumination and detection paths without placing the sample in a vacuum, by displacing said gases and moisture with at least another different gas so as to reduce attenuation of the at least one wavelength component, wherein the instrument supplies said at least another different gas along two different paths to the surface of the sample; and
  means for determining the characteristics of the surface from said at least one output signal.

147. The apparatus of claim 146, wherein said determining means determines information related to metrology of the sample.

148. The apparatus of claim 146, wherein said information is related to reflectivity, film thickness, index of refraction, and/or grating parameters of the sample, and/or change of phase of the radiation in the beam caused by the sample.

149. The apparatus of claim 148, wherein said grating parameters of the sample comprise critical dimension, wall angle, pitch, height and/or profile of gratings.

150. The apparatus of claim 146, wherein radiation in the beam is polarized.

151. The apparatus of claim 150, further comprising a device rotating a polarizer or compensator in the illumination and/or detection paths.

152. The apparatus of claim 146, wherein said optics varies an angle of incidence of the beam at a surface of the sample and said detector detects radiation from the surface at a corresponding angle.

153. The apparatus of claim 146, said optics illuminating the surface at different angles of incidence substantially simultaneously and said detector detects radiation from the surface along detection paths at different elevation angles from the surface substantially simultaneously.

154. The apparatus of claim 146, said optics illuminating the surface at different azimuthal angles substantially simultaneously and said detector detects radiation from the surface along detection paths at different azimuthal angles from the surface substantially simultaneously.

155. The apparatus of claim 146, said optics illuminating the surface with radiation of multiple wavelength components and the detector detects ellipsometric parameters of the sample.

156. The apparatus of claim 154, wherein said multiple wavelengths are in the visible, UV, DUV, VUV and/or IR ranges.

157. The apparatus of claim 146, wherein said optics comprises an objective focusing the beam to an area on the surface of the sample, said area having a dimension not more than about 200 microns.

158. The apparatus of claim 146, wherein said determining means determines information related to anomalies on or near the surface of the sample.

159. The apparatus of claim 146, said instrument directing a stream of gas to said at least a portion of each of the illumination and detection paths.

160. The apparatus of claim 159, wherein said instrument directs the stream of gas from a source of nitrogen or an inert gas.

161. The apparatus of claim 159, wherein said instrument directs the stream of gas towards a measurement area on the surface illuminated by the beam and causes laminar flow of the gas at or near the measurement area to be enhanced.

162. The apparatus of claim 159, wherein said instrument causes turbulent flow of the gas at or near the measurement area to be reduced.

163. The apparatus of claim 146, wherein said instrument comprises an envelope enclosing therein of at least a portion of each of the illumination and detection paths in a gas that contains less oxygen and moisture than those in an atmosphere surrounding said envelope.

164. The apparatus of claim 163, wherein said illuminating illuminates a measurement area on the surface, and wherein said envelope is at a pressure higher than that at a portion of each of the illumination and detection paths outside the envelope and near the measurement area on the surface.

165. The apparatus of claim 163, wherein said illuminating illuminates a measurement area on the surface, said envelope defining a hole therein, the illumination and detection paths passing through the hole, said instrument directing a stream of gas from the envelope through the hole towards the measurement area on the surface.

166. The apparatus of claim 165, the hole being within 1 cm from the surface.

167. The apparatus of claim 165, the hole having a tapered or funnel shape.

168. The apparatus of claim 167, the hole having a first and a second end where the first end is closer to the surface and is smaller than the second end.

169. The apparatus of claim 167, further comprising an objective in the envelope adjacent to the hole for focusing radiation in the illumination and detection paths.

170. The apparatus of claim 146, said instrument comprising a substantially sealed envelope containing at least part of said illumination path and at least part of said detection illumination path.

171. The method of claim 146, wherein said at least another different gas is supplied along a first path through an opening, and along second paths through orifices in a sheet-like radial flow away from the opening to the surface of the sample.

172. An optical method for detecting anomalies on or near a surface of a sample, comprising:
   illuminating the surface of the sample by a beam of radiation along an illumination path, radiation in said beam comprising at least one wavelength component in a vacuum ultraviolet (VUV) range;
   detecting radiation from the surface originating from the beam along a detection path to provide at least one output signal;
   reducing amount of ambient absorbing gases and moisture present in at least a portion of each of the illumination and detection paths without placing the sample in a vacuum, by displacing said gases and moisture with another gas that does not substantially absorb the at least one VUV wavelength component so as to reduce attenuation of the at least one VUV wavelength component, wherein the reducing includes supplying said another gas from a direction transverse to a direction normal to the surface of the sample and to at least one of the illumination and detection paths; and
   determining information related to anomalies on or near the surface from said at least one output signal.

173. The method of claim 172, wherein said detecting detects radiation in a bright field, dark field and/or double dark field arrangement.

174. The method of claim 172, further comprising causing the surface to be scanned by a beam of radiation when radiation from the beam is detected to determine information related to anomalies on or near an area of the surface of the sample.

175. The method of claim 174, wherein said causing causes the beam to scan a serpentine or spiral path on the surface.

176. The method of claim 172, wherein said detecting detects, separately and by means of different detection channels, radiation from the beam scattered by the surface in different directions that are arranged substantially symmetrically about a line normal to the surface.

177. The method of claim 172, wherein said beam is at an oblique angle to the surface of the sample, and wherein said detecting detects, separately and by means of different detection channels, radiation from the beam scattered by the surface within different ranges of azimuthal angles relative to the beam.

178. The method of claim 172, further comprising collecting radiation from the beam and scattered in different directions from the surface by means of a collector that is substantially symmetrical about a line normal to the surface.

179. The method of claim 172, wherein said detecting detects, separately and by means of different detection channels, radiation from the beam scattered by the surface in different directions that are at different elevation angles from the surface.

180. The method of claim 172, wherein said detecting detects separately two or more of the following: forward scattered radiation, back scattered radiation and radiation scattered in a direction normal to the surface.

181. The method of claim 172, wherein said illuminating comprises directing said beam at a normal direction to the surface of the sample.

182. The method of claim 172, wherein said illuminating comprises directing said beam at an oblique direction to the surface of the sample.

183. The method of claim 172, wherein said directing directs a stream of gas from a source of the gas that contains substantially no absorbing gas and moisture.

184. The method of claim 183, wherein said directing directs the stream of gas from a source of nitrogen or an inert gas.

185. The method of claim 183, wherein said directing is such that at least some contaminants and moisture at or near the measurement area on the surface are removed.

186. The method of claim 172, wherein said reducing comprises enclosing in an envelope of at least a portion of each of the illumination and detection paths in a gas that contains less oxygen and moisture than those in an atmosphere surrounding said envelope.

187. The method of claim 186, wherein said illuminating illuminates a measurement area on the surface, said method further comprising maintaining said envelope at a pressure higher than that at a portion of each of the illumination and detection paths outside the envelope and near the measurement area on the surface.

188. The method of claim 186, wherein said illuminating illuminates a measurement area on the surface, said envelope defining an opening, the illumination and detection paths passing through the opening, said reducing further comprising directing a stream of gas from the envelope through the opening towards the measurement area on the surface.

189. The method of claim 188, further comprising causing the opening to be within 1 cm from the surface.

190. The method of claim 186, wherein said sample is outside of the envelope during the illuminating, collecting, reducing and detecting.

191. The method of claim 172, wherein said illuminating employs illumination optics, said detecting employs detection optics and said reducing includes substantially sealing an envelope containing at least part of said illumination and detection optics.

192. A optical apparatus for measuring characteristics of a surface of a sample, comprising:
   optics illuminating the surface of the sample by a beam of radiation along an illumination path, radiation in said beam comprising at least one wavelength component in a vacuum ultraviolet range;
   a detector detecting radiation from the surface originating from the beam along a detection path to provide at least one output signal;
   an instrument reducing amount of ambient absorbing gases and moisture present in at least a portion of each of the illumination and detection paths without placing the sample in a vacuum, by displacing said gases and moisture with another different gas so as to reduce attenuation of the at least one wavelength component, wherein the instrument supplies said another different gas from a direction transverse to a direction normal to the surface of the sample and to at least one of the illumination and detection paths; and
   means for determining information related to anomalies on or near the surface from said at least one output signal.

193. The apparatus of claim 192, wherein said detector detects radiation in a bright field, dark field and/or double dark field arrangement.

194. The apparatus of claim 192, further comprising a device causing the surface to be scanned by a beam of radiation when radiation from the beam is detected to determine information related to anomalies on or near an area of the surface of the sample.

195. The apparatus of claim 194, wherein said device causes the beam to scan a serpentine or spiral path on the surface.

196. The apparatus of claim 194, wherein said device causes the surface to be moved without moving the optics and detector.

197. The apparatus of claim 192, wherein said detector comprises different detection channels, said detector comprising a plurality of detection channels detecting separately radiation from the beam scattered by the surface in different directions that are substantially symmetrically about a line normal to the surface.

198. The apparatus of claim 192, wherein said beam is at an oblique angle to the surface of the sample, said detector comprising a plurality of detection channels detecting separately radiation from the beam scattered by the surface within different ranges of azimuthal angles relative to the beam.

199. The apparatus of claim 192, further comprising a collector that is substantially symmetrical about a line normal to the surface collecting radiation from the beam and scattered in different directions from the surface, wherein the detector detects the radiation that is collected by the detector.

200. The apparatus of claim 192, wherein said detector comprises different detection channels, said detector comprising a plurality of detection channels detecting separately radiation from the beam scattered by the surface in different directions that are at different elevation angles from the surface.

201. The apparatus of claim 192, said detector comprising a plurality of detection channels detecting separately two or more of the following: forward scattered radiation, back scattered radiation and radiation scattered in a direction normal to the surface.

202. The apparatus of claim 192, said optics directing said beam at a normal direction to the surface of the sample.

203. The apparatus of claim 192, said optics directing said beam at an oblique direction to the surface of the sample.

204. The apparatus of claim 192, said instrument directing a stream of gas to said at least a portion of each of the illumination and detection paths from a source of the gas that contains substantially no absorbing gas and moisture.

205. The apparatus of claim 204, wherein said instrument directs the stream of gas from a source of nitrogen or an inert gas.

206. The apparatus of claim 204, wherein said instrument directs the stream of gas towards a measurement area on the surface illuminated by the beam.

207. The apparatus of claim 206, wherein said instrument causes laminar flow of the gas at or near the measurement area to be enhanced and turbulent flow of the gas at or near the measurement area to be reduced.

208. The apparatus of claim 206, wherein said instrument directs the gas towards the measurement area such that at least some contaminants and moisture at or near the measurement area on the surface are removed.

209. The apparatus of claim 192, wherein said instrument comprises an envelope enclosing therein of at least a portion of each of the illumination and detection paths in a gas that contains less oxygen and moisture than those in an atmosphere surrounding said envelope.

210. The apparatus of claim 209, wherein said illuminating illuminates a measurement area on the surface, and wherein said envelope is at a pressure higher than that at a portion of each of the illumination and detection paths outside the envelope and near the measurement area on the surface.

211. The apparatus of claim 209, wherein said illuminating illuminates a measurement area on the surface, said envelope defining a hole therein, the illumination and detection paths passing through the hole, said instrument directing a stream of gas from the envelope through the hole towards the measurement area on the surface.

212. The apparatus of claim 211, the hole being within 1 cm from the surface.

213. The apparatus of claim 211, the hole having a tapered or funnel shape.

214. The apparatus of claim 213, the hole having a first and a second end where the first end is closer to the surface and is smaller than the second end.

215. The apparatus of claim 211, the hole having two ends that are larger than a section of the hole between the two ends.

216. The apparatus of claim 211, wherein the hole is elongated in shape to accommodate illumination by the beam at an oblique angle to the surface.

217. The apparatus of claim 209, wherein said sample is outside of the envelope.

218. The apparatus of claim 192, wherein said optics comprises reflective optics.

219. The apparatus of claim 218, wherein said optics comprises at least one substantially spherical mirrored surface.

220. The apparatus of claim 192, wherein said optics comprises at least one lens comprising calcium fluoride.

221. The apparatus of claim 192, further comprising a collector that is collecting radiation from the beam and scattered by the surface, wherein the detector detects the radiation that is collected by the detector.

222. The apparatus of claim 221, wherein said collector comprises reflective optics.

223. The apparatus of claim 222, wherein said collector comprises at least one substantially paraboloidal or ellipsoidal mirrored surface.

224. The apparatus of claim 222, wherein said collector comprises at least one substantially ellipsoidal mirrored surface that has an axis that is substantially normal to the surface.

225. The apparatus of claim 221, wherein said collector comprises a plurality of collection devices arranged in a ring surrounding a portion of the surface illuminated by the beam.

226. The apparatus of claim 221, wherein said collector comprises at least one lens comprising calcium fluoride.

227. The apparatus of claim 192, said instrument comprising a substantially sealed envelope containing at least part of said illumination path and at least part of said detection illumination path.

* * * * *